(12) United States Patent
Scheinpflug et al.

(10) Patent No.: US 11,684,605 B2
(45) Date of Patent: Jun. 27, 2023

(54) LISINOPRIL COMPOSITIONS WITH AN INGESTIBLE EVENT MARKER

(71) Applicant: OTSUKA PHARMACEUTICAL CO., LTD., Tokyo (JP)

(72) Inventors: Kurt Scheinpflug, Dublin, CA (US); Nikhil Pargaonkar, Hayward, CA (US); Chris Dong, Redwood City, CA (US); Ai Ling Ching, San Francisco, CA (US); Dawn Adkin, Loughborough (GB)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 17/495,773

(22) Filed: Oct. 6, 2021

(65) Prior Publication Data

US 2022/0079919 A1 Mar. 17, 2022

Related U.S. Application Data

(63) Continuation of application No. 15/962,614, filed on Apr. 25, 2018, now Pat. No. 11,166,939.
(Continued)

(51) Int. Cl.
*G08B 21/04* (2006.01)
*A61K 31/401* (2006.01)
(Continued)

(52) U.S. Cl.
CPC ............ *A61K 31/401* (2013.01); *A61B 5/068* (2013.01); *A61B 5/073* (2013.01); *A61B 5/4833* (2013.01);
(Continued)

(58) Field of Classification Search
USPC ......... 424/464, 451, 465, 475, 45, 456, 462, 424/468, 474, 494, 497, 638, 641, 1.69;
(Continued)

(56) References Cited

U.S. PATENT DOCUMENTS 7,031,946 B1 4/2006 Tamai et al.
7,032,822 B2 4/2006 Waters
(Continued)

FOREIGN PATENT DOCUMENTS

JP 2008-539047 11/2008
JP 2009-537583 10/2009
(Continued)

OTHER PUBLICATIONS

Office Action dated Apr. 7, 2022, issued in the corresponding Taiwanese Patent Application No. 107114002, pp. 1-12.
(Continued)

*Primary Examiner* — Daniel Previl
(74) *Attorney, Agent, or Firm* — Pillsbury Winthrop Shaw Pittman LLP

(57) ABSTRACT

Provided herein are compositions for the ingestible administration of lisinopril. In some embodiments the compositions comprise lisinopril and silicon. In some embodiments, the compositions comprise lisinopril, silicon, magnesium metal, and copper (I) chloride. Also provided herein are apparatuses comprising the compositions provided herein. Also provided herein are methods for using the compositions and apparatuses provided herein.

11 Claims, 11 Drawing Sheets

Related U.S. Application Data

(60) Provisional application No. 62/490,010, filed on Apr. 25, 2017.

(51) Int. Cl.

| | | |
|---|---|---|
| *A61B 5/07* | (2006.01) | |
| *A61B 5/06* | (2006.01) | |
| *A61B 5/00* | (2006.01) | |
| *A61P 9/12* | (2006.01) | |
| *A61P 13/12* | (2006.01) | |
| *A61P 9/10* | (2006.01) | |
| *A61P 9/04* | (2006.01) | |
| *A61K 9/20* | (2006.01) | |
| *A61K 9/16* | (2006.01) | |
| *A61K 9/48* | (2006.01) | |
| *A61K 49/00* | (2006.01) | |

(52) U.S. Cl.
CPC .......... *A61B 5/4839* (2013.01); *A61K 9/1652* (2013.01); *A61K 9/2009* (2013.01); *A61K 9/2018* (2013.01); *A61K 9/2054* (2013.01); *A61K 9/2059* (2013.01); *A61K 9/485* (2013.01); *A61K 9/4816* (2013.01); *A61K 9/4825* (2013.01); *A61K 9/4858* (2013.01); *A61K 9/4866* (2013.01); *A61K 49/00* (2013.01); *A61P 9/04* (2018.01); *A61P 9/10* (2018.01); *A61P 9/12* (2018.01); *A61P 13/12* (2018.01); *A61B 2560/0204* (2013.01); *A61B 2560/0214* (2013.01); *A61B 2562/08* (2013.01); *A61B 2562/12* (2013.01)

(58) Field of Classification Search
USPC .... 514/23, 342, 635, 161, 212.07, 269, 370, 514/423, 458, 474, 543, 551, 674, 690, 514/725, 17.4, 176, 192, 197, 2.3, 20.6, 514/200, 251, 255.01, 26, 263.3, 28, 283, 514/290, 301, 304, 305, 31, 312, 317, 514/355, 356, 399, 43, 449, 457, 468, 514/510, 538, 547, 61, 7.4; 544/296, 1; 427/1, 2.1, 4, 7, 5, 8, 11, 446, 457, 58, 427/127, 133, 136, 140, 143, 144, 145, 427/154, 146, 157, 159, 161, 160, 162, 427/170, 171, 177, 180, 207.1, 209, 212, 427/223, 226, 230, 242, 240, 243, 248.1, 427/256, 289, 294, 299, 331, 399, 401, 427/420, 402, 421.1, 428.01, 429, 444, 427/430.1, 445, 900, 901, 903, 902; 340/539.12, 539.1, 539.11, 539.26, 545.3, 340/539.3, 579, 613, 636.11, 636.19, 340/5.52; 530/300, 321; 536/123.1, 6.5; 540/335, 57; 546/114, 318, 90; 548/341.5, 535; 549/458; 560/170, 173, 560/71, 80, 88, 1, 300, 301, 302, 303, 560/305, 304, 306, 307, 310, 311, 312, 560/316, 317, 318, 319, 330

See application file for complete search history.

(56) References Cited

U.S. PATENT DOCUMENTS

| | | |
|---|---|---|
| 7,035,818 B1 | 4/2006 | Brandy et al. |
| 7,035,877 B2 | 4/2006 | Markham et al. |
| 7,414,534 B1 | 8/2008 | Kroll et al. |
| 7,978,064 B2 | 7/2011 | Zdeblick et al. |
| 8,674,825 B2 | 3/2014 | Zdeblick et al. |
| 8,730,031 B2 | 5/2014 | Thompson et al. |
| 8,784,308 B2 | 7/2014 | Hafezi et al. |
| 8,802,183 B2 | 8/2014 | Frank et al. |
| 8,816,847 B2 | 8/2014 | Zdeblick et al. |
| 8,836,513 B2 | 9/2014 | Hafezi et al. |
| 8,847,766 B2 | 9/2014 | Zdeblick et al. |
| 8,912,908 B2 | 12/2014 | Berkman et al. |
| 9,271,897 B2 | 3/2016 | Costello et al. |
| 9,463,183 B1 | 10/2016 | Mosher et al. |
| 11,166,939 B2 * | 11/2021 | Scheinpflug ......... A61K 9/1652 |
| 2005/0131281 A1 | 6/2005 | Ayer et al. |
| 2006/0026217 A1 * | 2/2006 | Lindner .................. G11B 27/11 |
| 2006/0159742 A1 * | 7/2006 | Wilson .................... A61P 43/00 |
| | | 424/451 |
| 2006/0240105 A1 | 10/2006 | Devane et al. |
| 2007/0185199 A1 | 8/2007 | Ju et al. |
| 2008/0284599 A1 | 11/2008 | Zdeblick et al. |
| 2009/0196922 A1 * | 8/2009 | Guerrero ................ A61K 9/209 |
| | | 514/249 |
| 2009/0202635 A1 * | 8/2009 | Scott .................... A61K 9/7007 |
| | | 424/464 |
| 2010/0166857 A1 * | 7/2010 | Yan .......................... A61P 3/06 |
| | | 424/494 |
| 2010/0247632 A1 | 9/2010 | Dong et al. |
| 2010/0317562 A1 | 12/2010 | Paolella et al. |
| 2012/0059257 A1 | 3/2012 | Duck et al. |
| 2013/0030366 A1 | 1/2013 | Robertson et al. |
| 2013/0034606 A1 * | 2/2013 | Hallgren .................. A61P 5/50 |
| | | 514/23 |
| 2013/0115301 A1 | 5/2013 | Bele et al. |
| 2013/0129869 A1 | 5/2013 | Hafezi et al. |
| 2013/0345134 A1 | 12/2013 | Sauerberg et al. |
| 2014/0142149 A1 * | 5/2014 | Zhang ..................... A61P 1/18 |
| | | 514/380 |
| 2015/0064249 A1 * | 3/2015 | Folger .................. A61K 9/0056 |
| | | 514/212.07 |
| 2016/0345906 A1 | 12/2016 | Johnson et al. |
| 2016/0369058 A1 | 12/2016 | Zhang et al. |
| 2018/0047701 A1 | 2/2018 | Kalnitsky et al. |

FOREIGN PATENT DOCUMENTS

| | | |
|---|---|---|
| JP | 2013-523835 | 6/2013 |
| JP | 2015-506913 | 3/2015 |
| WO | 2005120502 | 12/2005 |
| WO | 2006/116718 | 11/2006 |
| WO | 2007/134870 | 11/2007 |
| WO | 2007134870 | 11/2007 |
| WO | 2009/010810 | 1/2009 |
| WO | 2010/132331 | 11/2010 |
| WO | 2011/127252 | 10/2011 |
| WO | 2013/078411 | 5/2013 |
| WO | 2014018454 | 1/2014 |
| WO | 2015119911 | 8/2015 |

OTHER PUBLICATIONS

International Search Report and Written Opinion issued in International PCT Application No. PCT/US2018/029386, dated Dec. 4, 2018.

Supplementary European Search Report for European Application No. 1879087.0, dated Nov. 25, 2020.

* cited by examiner

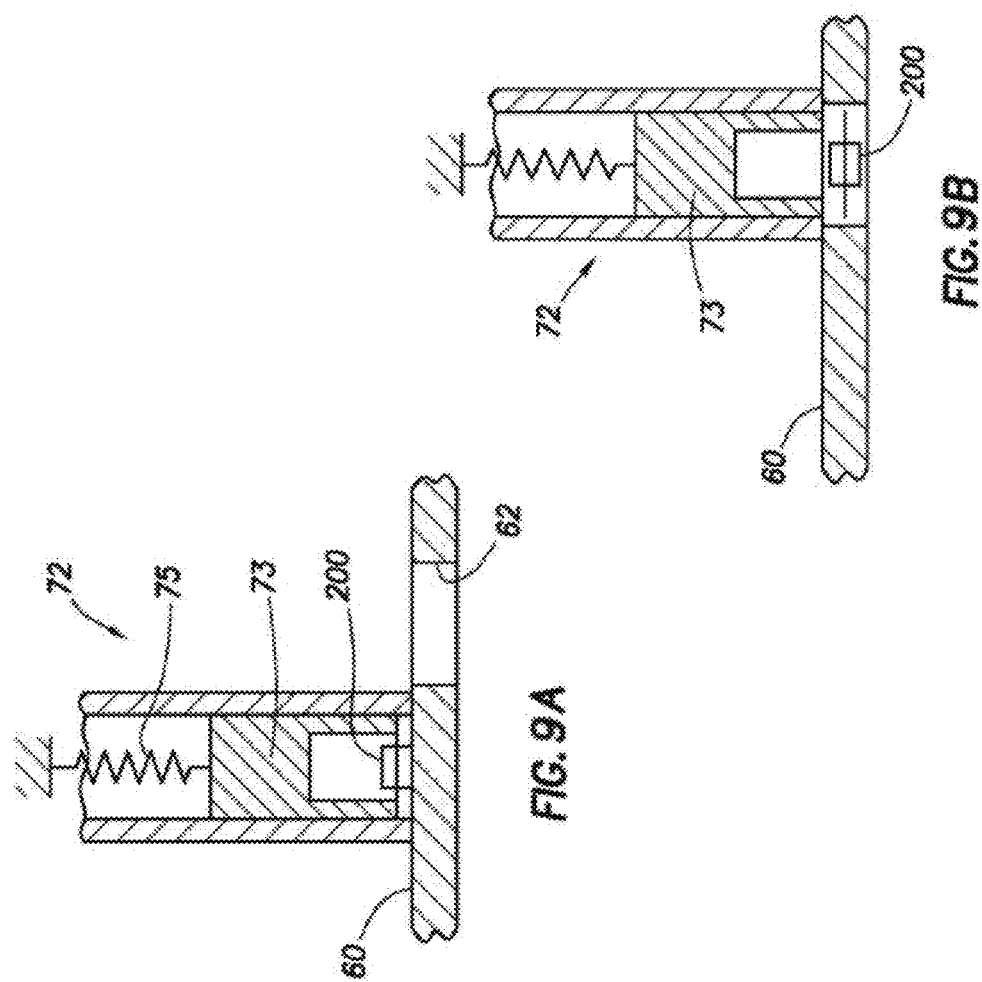
FIG. 9A
FIG. 9B
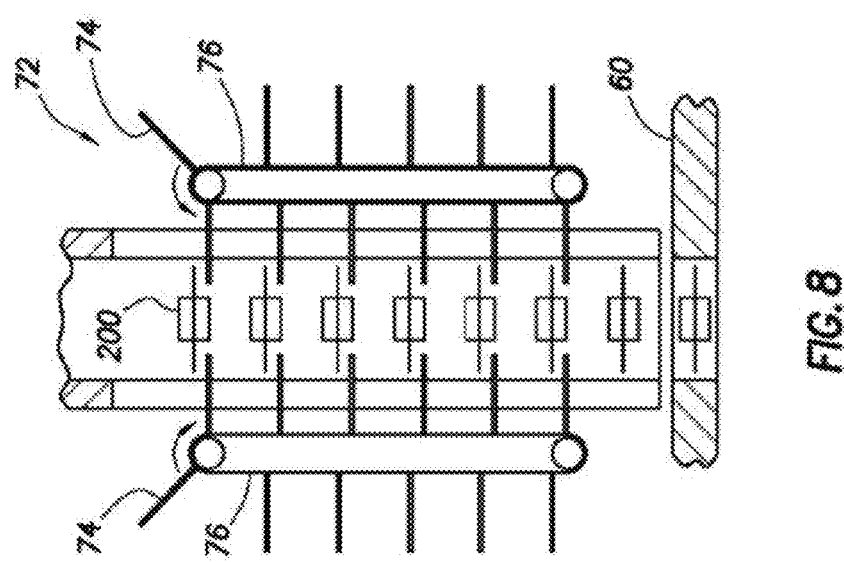
FIG. 8

LISINOPRIL COMPOSITIONS WITH AN INGESTIBLE EVENT MARKER

RELATED APPLICATIONS

This application claims priority to U.S. Provisional Application No. 62/490,010, filed Apr. 25, 2017, the entire content of which is incorporated herein by reference.

INTRODUCTION

Prescription medications are effective remedies for many patients when taken as instructed by the prescribing physician. However, studies have shown that, on average, about 50% of patients do not comply with prescribed medication regimens. A low rate of compliance with medication regimens results in a large number of hospitalizations and admissions to nursing homes every year. In the United States alone, it has recently been estimated that the cost resulting from patient non-compliance is reaching $100 billion annually.

One example situation where patient adherence is of particular importance is in the context of clinical studies. Non-adherence in the clinical trial setting has long-range consequences far beyond the few hundred patients who might be involved in a trial. To the extent that non-adherence occurs without a correction factor, it may have effects ranging from failure to gain Food and Drug Administration (FDA) approval to the necessity for increasing the recommended dose beyond that which would be required of a fully compliant population. Such an elevated dose could cause a higher incidence of side effects, which in turn may lead to further non-adherence.

Clinical studies typically enroll patients to undergo specific drug treatment regimens with the goal of testing hypotheses related to the effects of drug treatment on medically relevant clinical endpoints. Such studies might measure, for example, the relationship between alternative drug treatments with any of a wide variety of clinical endpoints, ranging from physiological, biochemical or psychological measurements, to manifestations of disease, patient survival or quality of life. In addition, drug treatments must also be related to any observed adverse events in an effort to identify rare adverse reactions or interactions with other medications.

The ability to reliably correlate highly specific drug treatment regimens, including dosage and administration methods, with both efficacy and safety depends to a great extent on the certainty of knowledge that every patient has followed the prescribed treatment regimen. Monitoring of patient adherence, including the exact time of administration for medications, is therefore of great value to patients and their physicians, as well as clinical trial sponsors and the pharmaceutical industry in general.

Various methods and apparatuses have been made available to improve patient compliance with prescribed regimens in efforts to improve patient health. Transdermal delivery systems combined with a unique biologically active ingredient provide sustained release formulations for the safe and efficacious transdermal administration of the unique biologically active ingredient to a subject through a body surface or membrane over a sustained time period for the treatment of various diseases. The transdermal route of parenteral delivery of drugs and other biologically active ingredients ("agents") has been proposed for a wide variety of systemically acting and locally acting agents on either a rate-controlled or non-rate-controlled basis. For example, sustained release formulations for the safe and efficacious administration of pharmaceutical active ingredients for the treatment of hypertension, congestive heart failure, and acute and chronic renal failure, among other things, have been proposed.

Additionally, different types of "smart" packaging devices have been developed. In some cases, such devices automatically dispense the appropriate pill. In other cases, there are electronic controls that detect and record when the pill is taken out of the box. However, improvements of patient compliance with prescription regimens have not addressed automatic tracking of oral administration (e.g., ingestion) of lisinopril (a.k.a., (2S)-1-[(2S)-6-amino-2-[[(1S)-1-carboxy-3-phenylpropyl]amino]hexanoyl]pyrrolidine-2-carboxylic acid, PRINIVIL®, ZESTRIL®) to a patient in need of administration thereof.

Thus, provided herein are methods of oral administration of lisinopril with an electronic circuitry system such as the electronic circuitry system developed by Proteus Digital Health, Inc. described in U.S. Pat. Nos. 7,978,064; 8,674,825; 8,730,031; 8,802,183; 8,816,847; 8,836,513; 8,847,766; and 8,912,908, the disclosures of which are incorporated in their entirety herein by reference. Also provided herein are delivery systems employing electronic circuits combined with specific formulations of lisinopril to provide different techniques for tracking oral delivery of the lisinopril to a patient in need of administration of lisinopril.

The present disclosure provides a unique composition of matter comprising the combination of the electronic circuitry comprising battery forming materials and specific formulations of lisinopril to confirm the delivery of the specific formulations of lisinopril. The present novel composition of matter also overcomes the unpredictable nature of combining various metals and salts with the specific formulations of lisinopril to provide an electronic delivery system that generates its own electrical power from a partial energy source comprised of dissimilar materials when exposed with the bodily fluids of a patient during the oral administration of the specific formulations of lisinopril.

The present disclosure relates generally to a composition of matter for the active monitoring of the ingestible administration of lisinopril. The composition of matter includes lisinopril, magnesium metal and copper chloride (e.g., copper (I) chloride, CuCl, or cuprous chloride). These materials and the final complete tablet formulation were chosen for a variety of reasons. First, we were able to show that this specific formulation of copper chloride, magnesium metal, connected by silicon that is conductive when wet, do not appreciably alter the chemical composition of lisinopril when ingested even after being stored after manufacturing for an extended period of time. Second, the combination of lisinopril with copper chloride, magnesium metal and silicon does not facilitate the reaction of copper chloride and magnesium metal. Such a reaction, for example while being stored after manufacturing and before delivery to a patient, could cause the magnesium metal or copper chloride to react; the bi-products of such a reaction could change the chemical composition of the lisinopril; or, if all or most of the magnesium metal or copper chloride are reacted, render the ingestion sensor powerless and inert when ingested. Thus, uniquely, a formulation containing the lisinopril and the materials that make up the ingestion sensor must be found and proven to not adversely affect the purpose of the other.

An example of how this conflict has manifested itself in early experiments demonstrates this unique challenge: early experiments were made without any lisinopril in the tablet— just the ingestion sensor and "placebo" formulation of inert materials. A placebo pill without an embedded ingestion sensor can sit in an open container in a hot, humid bathroom for months without changing its ultimate performance. Many—but not all—pharmaceuticals or dietary supplements such as vitamins can be stored in a similar manner without adversely affecting their effectiveness. When in our early experiments we added ingestion sensors to such "placebo" tablets, however, we found that the partial power source made of copper chloride (e.g., copper (I) chloride, CuCl, or cuprous chloride) and magnesium metal would react with each other—effectively "discharging" the biogalvanic potential—before the placebo-with-ingestion-sensor tablet was ingested. Further, with some active ingredients, the relaxation of polymer skirt size could cause the tablet to break up into pieces. Thus, the process of discovering and validating a precise formulation including lisinopril, magnesium metal, copper chloride and silicon that allows all of these materials to stably co-exist for an extended period of time is a unique challenge that depends upon the reactivity of the lisinopril as formulated with the pair of electrochemically active materials, magnesium metal and copper chloride. More specifically, the present disclosure relates to compositions used in an apparatus for automatic (i.e. electronic) identification of ingestion, i.e., oral administration, of lisinopril.

SUMMARY

According to one aspect of the present disclosure, a composition of matter for the ingestible administration of lisinopril is provided. In some embodiments, the composition comprises lisinopril, magnesium metal, copper chloride, and silicon. In some embodiments, the composition comprises lisinopril; and silicon having a mass equivalent to a silicon substrate having dimensions of between 0.5×0.5×0.5 mm (0.125 $mm^3$) and 3×3×1 mm (09 $mm^3$), or more particularly, roughly 1.0×1.0×0.3 mm (0.3 $mm^3$).

According to one aspect of the present disclosure, an apparatus is provided. The apparatus comprises lisinopril; a substrate with a first surface and a second surface; a partial power source comprising a first material provided on the first surface of the substrate, wherein the first material is magnesium metal, and a second material provided on the second surface of the substrate, wherein the second material is copper chloride (e.g., copper (I) chloride, CuCl, or cuprous chloride), wherein the partial power source is configured to generate power upon contact of the first material and the second material with a fluid; and a control unit electronically coupled with the partial power source, wherein the control unit is configured to be activated by receiving the power from the partial power source and to encode information in a current flow through the fluid.

BRIEF DESCRIPTION OF THE FIGURES

The features of the various aspects of the present disclosure are set forth with particularity in the appended claims. The various aspects, both as to organization and methods of operation, together with advantages thereof, may, however best be understood by reference to the following description, taken in conjunction with the accompanying drawings as follows:

FIG. 8 is a close-up view of a portion of a feeder assembly that can be used with the apparatus of FIG. 5 in accordance with another aspect of the present disclosure.

FIG. 9A is a close-up view of a portion of a feeder assembly that can be used with the apparatus of FIG. 5 in accordance with another aspect of the present disclosure.

FIG. 9B is a close-up view of a portion of the feeder assembly shown in FIG. 9A at an advanced stage in the loading process, according to one aspect of the present disclosure.

DETAILED DESCRIPTION

Figure 1:
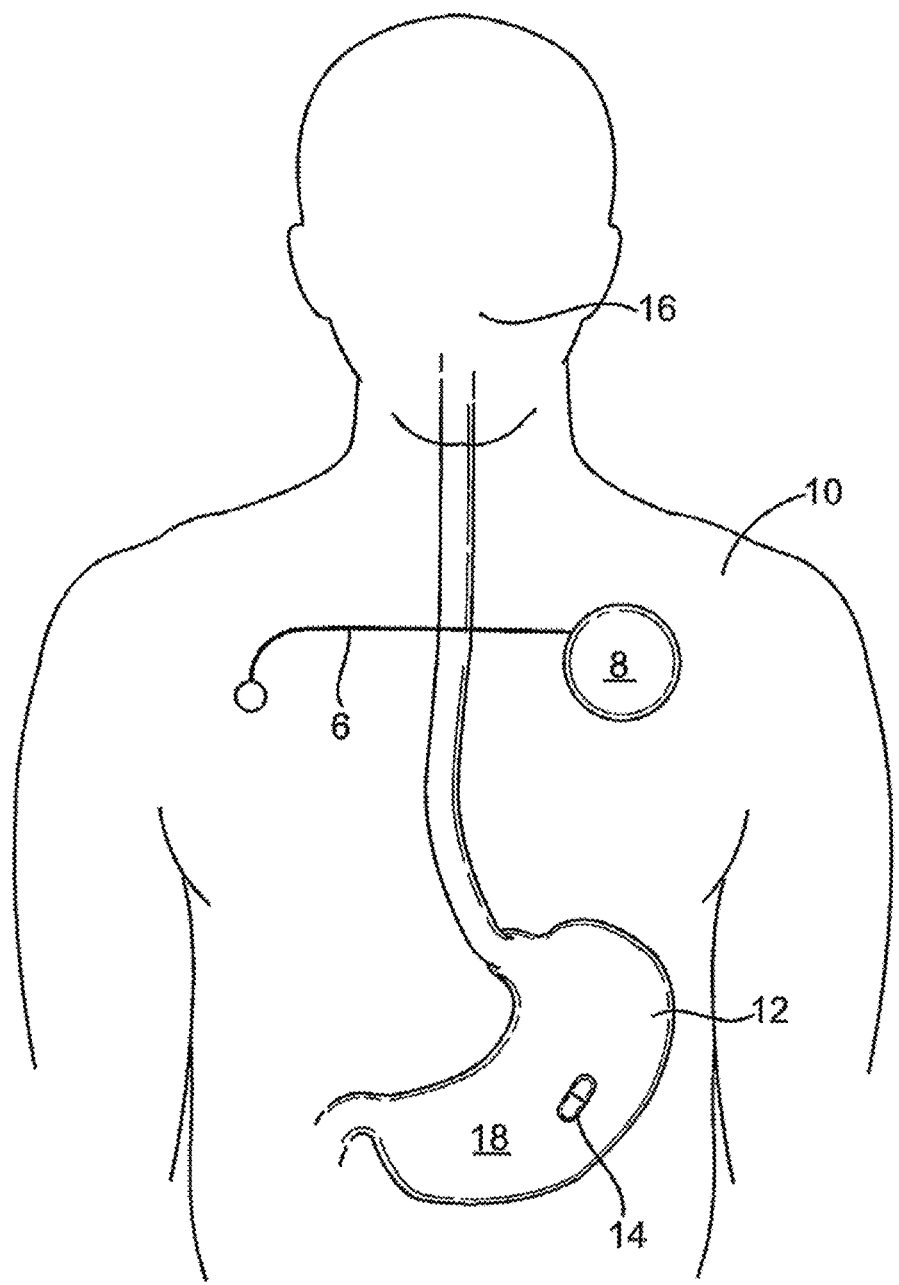
FIG. 1 is a diagrammatic, exemplary representation of the pill embodiment of the present disclosure, according to one aspect of the present disclosure.

The drawings and descriptions provided herein should be regarded as illustrative in nature and not restrictive.

Any one or more of the teachings, expressions, aspects, examples, etc. described herein may be combined with any one or more of the other teachings, expressions, aspects, examples, etc. that are described herein. The following described teachings, expressions, aspects, examples, etc. should, therefore, not be viewed in isolation relative to each other. Various suitable ways in which the teachings herein may be combined will be readily apparent to those of ordinary skill in the art in view of the teachings herein. Such modifications and variations are intended to be included within the scope of the claims.

The present disclosure provides the clinician an important new tool in their therapeutic armamentarium: automatic detection and identification of pharmaceutical agents actually delivered into the body. The applications of this new information device and system are multi-fold. By example, when used in concert with other medical sensing devices, correlation between drug delivery, batch and dosage can be correlated to a physiological response. In this manner, optimal pharma-therapeutic regimens may be formulated by the clinician.

Assessment of medications is made possible by the present disclosure without resort to awaiting overt clinical sequel of treatment, many of which can be seriously adverse. By example, positive effects would be quickly ascertainable without being obscured by more random factors. Negative responses, such as changes in blood pressure, would become clearly evident as drug related or independent above background physiologic variation.

The ability to document the ingestion of a drug or other actual exposure of the body to a medication has many important clinical applications. In the simplest form, this technique provides accurate data of when a pill has been taken and which pill has been taken. This allows the precise determination of which pill was taken at a specific point in time. Such monitoring capability assures patients are taking the prescribed medication correctly. This information avoids the potential for over-prescription of medications that are not actually being taken.

The present disclosure provides the clinician an accurate dose response curve showing the response to a medication and the timing of the ingestion of the pill. Such data has many applications. For instance, the clinician now has the ability to determine which patients have no response to the medicine in the pill. In a study situation, such patients can be removed from a study or a test of the clinical utility of a certain medication. This provides that only people who have a beneficial response to a certain medication are retained in the trial. This feature will improve the efficacy of medications and to reduce the amount of medications that people take that are not being useful. It may also be used in trials to determine which patients actually consumed the medicine, and which did not.

In more standard clinical environments, this unique data allows careful selection and titration of drug administration without resorting to more overt physical symptoms to ascertain contraindications, efficacy, and optimal dosage levels. The present disclosure provides a record for emergency room technicians or doctors when a patient is admitted to a hospital so that the patient's status can be accurately ascertained. Dosage events within the last hour or day prior to admission, and the identity of the last medication, will be immediately available.

The clinician obtains this information through simple interrogation of the implanted or portable device. This device would tell them without any uncertainty what pills have been taken.

A "smart box" may be provided that can interrogate each pill and ascertain its address. The box can write a distinctive product number or product code so that every single pill ever made is provided with a unique identifier. Fuses, for example, may be selectively destroyed so the addresses may be detected electrically or optically. The present disclosure makes it possible to identify precisely who bought such a pill from the authorized pharmacist.

Embodiments of the disclosure may include compositions having an identifier stably associated therewith. In certain embodiments, the compositions may be disrupted upon administration to a subject. As such, in certain embodiments, the compositions may be physically broken, e.g., dissolved, degraded, eroded, etc., following delivery to a body, e.g., via ingestion. The compositions of these embodiments may be distinguished from devices that are configured to be ingested and survive transit through the gastrointestinal tract substantially, if not completely, intact. While the compositions of these embodiments may be themselves disrupted upon administration, components of the composition, e.g., the identifier, may survive transit of the gastrointestinal tract, e.g., as described in greater detail below.

In certain embodiments, the compositions may include a lisinopril/carrier component and an identifier. Each of these different components is reviewed separately in greater detail below.

Lisinopril/Carrier Component

The subject compositions may include a lisinopril/carrier component. The lisinopril/carrier component may be a solid, which has an amount of lisinopril, e.g., a dosage, present in a pharmaceutically acceptable carrier. The lisinopril/carrier component may be referred to as a "dosage formulation."

As used herein, the term "IEM TAB" refers to ingestible-event-marker-in-tablet, an identifier directly compressed within a tablet comprised of a drug-containing blend. In some embodiments, the IEM TAB may be about 45 to about 580 mg, about 50 mg, about 100 mg, about 200 mg, or about 550 mg.

As used herein, the term "SP TAB" refers to sensor-pill-in-tablet, an identifier compressed within a tablet comprised of excipients (without drug) that is further compressed into a drug containing blend utilizing a core tablet press (e.g., dry coat or mantle coat process). In some embodiments, the SP TAB may be about 225 to about 635 mg, about 235 mg, about 255 mg, or about 605 mg.

As used herein, the term "SP CAP" refers to sensor pill-in-capsule, an identifier compressed within a tablet comprised of excipients (without drug) that is further encapsulated with a drug-containing powder (e.g., dry blend or granule), pellet, bead, mini-tablet, or tablet. In some embodiments, the SP CAP may be about 225 to about 615 mg, about 235 mg, about 285 mg, about 385 mg, or about 585 mg.

Lisinopril Compositions

"Lisinopril" produces a physiological result, e.g., a beneficial or useful result, upon contact with a living organism, e.g., a mammal, such as a human. Compositions provided herein comprise a lisinopril. Lisinopril may be referred to as, for example, (2S)-1-[(2S)-6-amino-2-[[(1S)-1-carboxy-3-phenylpropyl]amino]hexanoyl]pyrrolidine-2-carboxylic acid, PRINIVIL®, or ZESTRIL®.

Unless otherwise indicated, any reference to lisinopril herein by structure or name includes: pharmaceutically acceptable salts; alternate solid forms, such as polymorphs, solvates, hydrates, etc.; tautomers; deuterium-modified lisinoprils; or combinations thereof.

In some aspects, provided herein is a composition comprising lisinopril. In some embodiments, the composition is an ingestible event marker composition comprising lisinopril.

In some embodiments, lisinopril as used herein may be present as a pharmaceutically acceptable salt (e.g., a pharmaceutically acceptable salt found in Remington's Pharmaceutical Sciences, Mace Publishing Company, Philadelphia, Pa., 17th ed. 1985).

Lisinopril is an active pharmaceutical ingredient found in ZESTRIL® tablets to treat high blood pressure (hypertension) in adults and children above 6 years of age. In some embodiments, lisinopril as used herein is a lisinopril dihydrate.

Lisinopril exhibits polymorphism. It has amorphous and crystalline hydrate forms such as lisinopril amorphous form, lisinopril monohydrate (form-I), lisinopril monohydrate (form-II), and lisinopril dihydrate. In some embodiments, lisinopril as used herein is a lisinopril polymorph. In some embodiments, lisinopril as used herein is lisinopril amorphous form, lisinopril monohydrate (form-I), lisinopril monohydrate (form-II), or lisinopril dihydrate.

In some embodiments, the lisinopril compositions provided herein further comprise (2S)-2-[(3S,8aR)-3-(4-aminobutyl)-1,4-dioxo-6,7,8,8a-tetrahydro-3H-pyrrolo[1,2-a]pyrazin-2-yl]-4-phenylbutanoic acid (i.e. lisinopril diketopiperazine or lisinopril dihydrate impurity D), wherein the (2S)-2-[(3S,8aR)-3-(4-aminobutyl)-1,4-dioxo-6,7,8,8a-tetrahydro-3H-pyrrolo[1,2-a]pyrazin-2-yl]-4-phenylbutanoic acid is present in an amount of not more than about 0.001-0.30% by weight (e.g., not more than about 0.01-0.30%, 0.10-0.30%, 0.10-0.25%, 0.15-0.30%, 0.20-0.30%, 0.25-0.30%, 0.001%, 0.01%, 0.10%, 0.15%, 0.20%, 0.25%, or 0.30%). In some embodiments, the (2S)-2-[(3S,8aR)-3-(4-aminobutyl)-1,4-dioxo-6,7,8,8a-tetrahydro-3H-pyrrolo[1,2-a]pyrazin-2-yl]-4-phenylbutanoic acid is present in an amount of not more than about 0.001-0.30% by weight (e.g., not more than about 0.01-0.30%, 0.10-0.30%, 0.10-0.25%, 0.15-0.30%, 0.20-0.30%, 0.25-0.30%, 0.001%, 0.01%, 0.10%, 0.15%, 0.20%, 0.25%, or 0.30%) at about six months after the composition was prepared.

In some embodiments, the lisinopril compositions provided herein further comprise (2S)-2-[(3S,8aR)-3-(4-aminobutyl)-1,4-dioxo-6,7,8,8a-tetrahydro-3H-pyrrolo[1,2-a]pyrazin-2-yl]-4-phenylbutanoic acid, wherein the (2S)-2-[(3S,8aR)-3-(4-aminobutyl)-1,4-dioxo-6,7,8,8a-tetrahydro-3H-pyrrolo[1,2-a]pyrazin-2-yl]-4-phenylbutanoic acid is present in an amount of not more than about 0.001-0.10% by weight (e.g., not more than about 0.01-0.10%, 0.01-0.05%, 0.05-0.10%, 0.001%, 0.01%, 0.02%, 0.03%, 0.04%, 0.05%, 0.06% 0.07%, 0.08%, 0.09%, or 0.10%). In some embodiments, the (2S)-2-[(3S,8aR)-3-(4-aminobutyl)-1,4-dioxo-6,7,8,8a-tetrahydro-3H-pyrrolo[1,2-a]pyrazin-2-yl]-4-phenylbutanoic acid is present in an amount of not more than about 0.001-0.10% by weight (e.g., not more than about 0.01-0.10%, 0.01-0.05%, 0.05-0.10%, 0.001%, 0.01%, 0.02%, 0.03%, 0.04%, 0.05%, 0.06% 0.07%, 0.08%, 0.09%, or 0.10%) at about six months after the composition was prepared.

In some embodiments, the lisinopril compositions provided herein comprise less than about 0.001%, independently, of 2-amino-4-phenylbutanoic acid (lisinopril impurity A), 4-Methylbenzenesulphonic acid (lisinopril impurity B), (2S)-2-[(3S,8aS)-3-(4-Aminobutyl)-1,4-dioxohexahydropyrrolo[1,2-a]pyrazin-2(1H)-yl]-4-phenylbutanoic acid (lisinopril impurity C), 2S)-1-[(2S)-6-Amino-2-[[(1R)-1-carboxy-3-phenylpropyl]amino]hexanoyl] pyrrole-2-carboxylic acid (lisinopril impurity E), (2S)-1-[(2S)-6-amino-2-[[(1S)-1-carboxy-3-cyclohexylpropyl]amino] hexanoyl] pyrrole-2-carboxylic acid (lisinopril impurity F), (S)-1-((S)-6-((S)-2-(((S)-6-Amino-1-((S)-2-carboxypyrrolidin-1-yl)-1-oxohexan-2-yl)amino)-4-phenylbutanamido)-2-(((S)-1-carboxy-3-phenylpropyl)amino)hexanoyl)pyrrolidine-2-carboxylic Acid (lisinopril impurity G), lisinopril dimer impurity H ($C_{37}H_{53}N_5O_8$), or lisinopril impurity I ($C_{31}H_{41}N_3O_7$). In some embodiments, the lisinopril compositions provided herein comprise less than about 0.001%, independently, of 2-amino-4-phenylbutanoic acid (lisinopril impurity A), 4-Methylbenzenesulphonic acid (lisinopril impurity B), (2S)-2-[(3S,8aS)-3-(4-Aminobutyl)-1,4-dioxohexahydropyrrolo[1,2-a]pyrazin-2(1H)-yl]-4-phenylbutanoic acid (lisinopril impurity C), 2S)-1-[(2S)-6-Amino-2-[[(1R)-1-carboxy-3-phenylpropyl]amino]hexanoyl] pyrrole-2-carboxylic acid (lisinopril impurity E), (2S)-1-[(2S)-6-amino-2-[[(1S)-1-carboxy-3-cyclohexylpropyl]amino] hexanoyl]pyrrole-2-carboxylic acid (lisinopril impurity F), (S)-1-((S)-6-((S)-2-(((S)-6-Amino-1-((S)-2-carboxypyrrolidin-1-yl)-1-oxohexan-2-yl)amino)-4-phenylbutanamido)-2-(((S)-1-carboxy-3-phenylpropyl)amino)hexanoyl)pyrrolidine-2-carboxylic Acid (lisinopril impurity G), lisinopril dimer impurity H ($C_{37}H_{53}N_5O_8$), and lisinopril impurity I ($C_{31}H_{41}N_3O_7$).

As indicated above, in some embodiments a composition including lisinopril provided herein may be present in a pharmaceutically acceptable vehicle or carrier, e.g., as described below. In some embodiments, the lisinopril may be present in an amount of from about 0.1% to about 90% by weight, e.g., from about 0.1% to about 30% by weight, e.g., from about 1% to about 30% by weight, e.g., from about 1% to about 20% by weight, e.g. about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20% by weight of the compositions, or a range bounded by any two of these values.

In some embodiments, the composition comprises about 5 to about 80 mg of lisinopril. In some embodiments, the composition comprises about 5, 10, 15, 20, 25, 30, 35, 40, 45, 50, 55, 60, 65, 70, 75, 80 mg, or a range bounded by any two of these values. In some embodiments, the composition comprises about 40 mg of lisinopril. In some embodiments, the composition comprises about 10 mg of lisinopril.

In some embodiments, the composition is encapsulated within a capsule. In some embodiments, the capsule is a gelatin capsule. In some embodiments, the capsule is a hydroxypropyl methyl cellulose capsule. In some embodiments, the capsule is a size 2, 1, 0, 0 el, 00, 00 el, or 000 capsule.

In some embodiments, the composition further comprises silicon, magnesium, copper (I) chloride, ethyl cellulose, and hydroxypropyl cellulose.

In some embodiments, the composition further comprises silicon, aluminum, silicon dioxide, silicon nitride, titanium, titanium-tungsten, gold, magnesium, copper (I) chloride, hydroxypropyl cellulose, ethyl cellulose, triethyl citrate, or a combination thereof. In some embodiments, the silicon, aluminum, silicon dioxide, silicon nitride, titanium, titanium-tungsten, gold, magnesium, copper (I) chloride, hydroxypropyl cellulose, ethyl cellulose, triethyl citrate, or a combination thereof is in an identifier.

In some embodiments, the identifier comprises an integrated circuit, a wafer, and a skirt film. In some embodiments, the identifier further comprises a coating that coats the circuit, wafer and skirt film. In some embodiments, the identifier is about 0.5% to about 5% w/w of the composition. In some embodiments, the identifier is about 0.5% w/w of the composition. In some embodiments, the identifier is about 1% w/w of the composition. In some embodiments, the identifier is about 1.5% w/w of the composition. In some embodiments, the identifier is about 2% w/w of the composition. In some embodiments, the identifier is about 2.5% w/w of the composition. In some embodiments, the identifier is about 3% w/w of the composition. In some embodiments, the identifier is about 3.5% w/w of the composition. In some embodiments, the identifier is about 4% w/w of the composition. In some embodiments, the identifier is about 4.5% w/w of the composition. In some embodiments, the identifier is about 5% w/w of the composition. In some embodiments, the identifier is about 6%, 7%, 8%, 9% or 10% w/w of the composition. In some embodiments, the identifier is about 3, 4, 5, 6, 7, 8, 9, or 10 mg. In some embodiments, the identifier is about 3.8 to about 4.1 mg. In some embodiments, the identifier is about 3.92 mg.

In some embodiments, the integrated circuit comprises silicon, aluminum, silicon dioxide, silicon nitride, or a combination thereof. In some embodiments, the integrated circuit comprises silicon, aluminum, silicon dioxide, and silicon nitride.

In some embodiments, the wafer comprises titanium, titanium-tungsten, gold, magnesium, copper (I) chloride, hydroxypropyl cellulose, or a combination thereof. In some embodiments, the wafer comprises titanium, titanium-tungsten, gold, magnesium, copper (I) chloride, and hydroxypropyl cellulose.

In some embodiments, the skirt film comprises ethyl cellulose, hydroxypropyl cellulose, triethyl citrate, or a combination thereof. In some embodiments, the skirt film comprises ethyl cellulose, hydroxypropyl cellulose, and triethyl citrate.

In some embodiments, the coating comprises hydroxypropyl cellulose.

In some embodiments, the identifier comprises about 15 to about 25% w/w integrated circuit. In some embodiments, the identifier comprises about 18 to about 21% w/w integrated circuit. In some embodiments, the identifier comprises about 19.5% w/w integrated circuit. In some embodiments, the identifier comprises about 2 to about 4% w/w wafer. In some embodiments, the identifier comprises about 3.1% w/w wafer. In some embodiments, the identifier comprises about 65 to about 75% w/w skirt film. In some embodiments, the identifier comprises about 70 to about 73% w/w skirt film. In some embodiments, the identifier comprises about 71.5% w/w skirt film. In some embodiments, the identifier comprises about 4 to about 7% w/w coating. In some embodiments, the identifier comprises about 5.5 to about 6.5% w/w coating. In some embodiments, the identifier comprises about 5.9% w/w coating.

In some embodiments, the composition further comprises about 0.5% to about 1% w/w magnesium stearate. In some embodiments, the composition comprises about 0.5% w/w magnesium stearate. In some embodiments, the composition comprises about 1% w/w magnesium stearate.

In some embodiments, the composition further comprises about 5% to about 20% w/w pregelatinized starch. In some embodiments, the composition further comprises about 5% to about 10% w/w pregelatinized starch. In some embodiments, the composition further comprises about 10% to about 20% w/w pregelatinized starch. In some embodiments, the composition comprises about 5% w/w pregelatinized starch. In some embodiments, the composition comprises about 10% w/w pregelatinized starch. In some embodiments, the composition comprises about 15% w/w pregelatinized starch. In some embodiments, the composition comprises about 20% w/w pregelatinized starch.

In some embodiments, the composition further comprises about 15% to about 30% w/w microcrystalline cellulose. In some embodiments, the composition further comprises about 15% w/w microcrystalline cellulose. In some embodiments, the composition further comprises about 30% w/w microcrystalline cellulose.

In some embodiments, the composition further comprises about 0% to about 2% w/w croscarmellose sodium. In some embodiments, the composition comprises about 1% to about 2% w/w croscarmellose sodium. In some embodiments, the composition comprises about 2% w/w croscarmellose sodium.

In some embodiments, the composition further comprises about 20% to about 30% w/w mannitol (e.g., 50 μm). In some embodiments, the composition comprises about 24% to about 25% w/w mannitol (e.g., 50 μm). In some embodiments, the composition comprises about 24.6% w/w mannitol (e.g., 50 μm).

In some embodiments, the composition further comprises about 15% to about 30% w/w dicalcium phosphate dihydrate. In some embodiments, the composition further comprises about 15% w/w dicalcium phosphate dihydrate. In some embodiments, the composition further comprises about 30% w/w dicalcium phosphate dihydrate.

In some embodiments, the lisinopril is present in the composition in about 7.3% w/w.

In some embodiments, the composition further comprises about 0.10% to about 0.20% w/w iron oxide yellow. In some embodiments, the composition comprises about 0.10% to about 0.15% w/w iron oxide yellow. In some embodiments, the composition comprises about 0.15% to about 0.20% w/w iron oxide yellow. In some embodiments, the composition comprises about 0.15% w/w iron oxide yellow.

In some embodiments, the composition further comprises 0.5% to about 1% w/w magnesium stearate, 0% to about 2% w/w croscarmellose sodium, and an ingestible event marker.

In some embodiments, the lisinopril is in a granule comprising: the lisinopril, dicalcium phosphate dihydrate, mannitol (e.g., 180 μm), and pregelatinized starch. In some embodiments, the granule further comprises iron oxide yellow or water, or both.

In some embodiments, the granule comprises about 8% to about 14% w/w lisinopril. In some embodiments, the granule comprises about 10% to about 12% w/w lisinopril. In some embodiments, the granule comprises about 10.3% to about 11.3% w/w lisinopril. In some embodiments, the granule comprises about 10.3% w/w lisinopril. In some embodiments, the granule comprises about 11.2% w/w lisinopril. In some embodiments, the composition comprises about 40 mg of lisinopril.

In some embodiments, the granule comprises about 14% to about 18% w/w dicalcium phosphate dihydrate. In some embodiments, the granule comprises about 15% to about 17% w/w dicalcium phosphate dihydrate. In some embodiments, the granule comprises about 15.4% to about 16.9% w/w dicalcium phosphate dihydrate. In some embodiments, the granule comprises about 15.5% w/w dicalcium phosphate dihydrate. In some embodiments, the granule comprises about 16.9% w/w dicalcium phosphate dihydrate.

In some embodiments, the granule comprises about 55% to about 65% w/w mannitol (e.g., 180 μm). In some embodiments, the granule comprises about 57% to about 62% w/w mannitol (e.g., 180 μm). In some embodiments, the granule comprises about 58% to about 61% w/w mannitol (e.g., 180 μm). In some embodiments, the granule comprises about 58% ow/w mannitol (e.g., 180 μm). In some embodiments, the granule comprises about 61% w/w mannitol (e.g., 180 μm). In some embodiments, the granule comprises about 58.6% w/w mannitol (e.g., 180 μm). In some embodiments, the granule comprises about 61.5% w/w mannitol (e.g., 180 μm).

In some embodiments, the granule comprises about 9% to about 18% w/w pregelatinized starch. In some embodiments, the granule comprises about 10% to about 17% w/w pregelatinized starch. In some embodiments, the granule comprises about 11% to about 16% w/w pregelatinized starch. In some embodiments, the granule comprises about 11% w/w pregelatinized starch. In some embodiments, the granule comprises about 11.2% w/w pregelatinized starch.

In some embodiments, the granule comprises about 16% w/w pregelatinized starch. In some embodiments, the granule comprises about 15.5% w/w pregelatinized starch.

In some embodiments, the granule comprises about 0.10% to about 0.20% w/w iron oxide yellow. In some embodiments, the granule comprises about 0.10% to about 0.15% w/w iron oxide yellow. In some embodiments, the granule comprises about 0.15% to about 0.20% w/w iron oxide yellow. In some embodiments, the granule comprises about 0.15% w/w iron oxide yellow.

In some embodiments, the granule comprises about 10.3% w/w lisinopril, about 15.5% w/w dicalcium phosphate, about 58.6% w/w mannitol (e.g., 180 μm), and about 15.5% w/w pregelatinized starch. In some embodiments, the granule comprises about 10.3% w/w lisinopril, about 15.5% w/w dicalcium phosphate, about 58.6% w/w mannitol (e.g., 180 μm), about 15.5% w/w pregelatinized starch, and about 0.15% w/w iron oxide yellow.

In some embodiments, the granule comprises about 11.2% w/w lisinopril, about 16.9% w/w dicalcium phosphate, about 60.5% w/w mannitol (e.g., 180 μm), and about 11.2% w/w pregelatinized starch. In some embodiments, the granule comprises about 11.2% w/w lisinopril, about 16.9% w/w dicalcium phosphate, about 60.5% w/w mannitol (e.g., 180 μm), about 11.2% w/w pregelatinized starch, and about 0.15% w/w iron oxide yellow.

In some embodiments, the composition comprises about 4.5% to about 18.5% w/w lisinopril (e.g., about 5, 10, or 18.2% w/w), about 13.0% to about 16.0% ow/w dicalcium phosphate (e.g., about 28.0, 30.5, 13.2, or 14.3% w/w), about 10.5% to about 59.0% w/w mannitol (e.g., about 22.9, 25.6, 47.5, or 51.4% w/w), about 4.5% to about 20.5% w/w pregelatinized starch (e.g., about 5, 20, or 22% w/w), about 0% to about 30.0% w/w microcrystalline cellulose (e.g., about 0 or 16% w/w), about 0% to about 2.5% w/w croscarmellose sodium (e.g., about 0 or 2% w/w), about 0% to about 0.20% w/w iron oxide (e.g., about 0.14 or 0.15% w/w), about 0% to about 0.30% w/w FD&C yellow #6 (e.g., about 0% w/w), wherein the lisinopril, dicalcium phosphate, mannitol, pregelatinized starch, microcrystalline cellulose, croscarmellose sodium, iron oxide, and FD&C yellow #6 are in a granule, and about 0% to about 10.5% w/w extragranular pregelatinized starch (e.g., about 0 or 10% w/w), and about 0% to about 1.5% w/w extra granular magnesium stearate (e.g., about 1% w/w).

In some embodiments, the composition comprises a composition provided in Table 1, Table 3 (e.g., B5, A5, A4, A4+AcDiSol, A4+Starch, A5+Starch, A6a, A6b, B6, A4a, A4b, A4c, A4d, A4e, A4f, A5a, A5b), or Table 4 (e.g., B6 (F), B6 (P), B7 (P), A6-a (P), or A6-b (F)). In some embodiments, the composition comprises a core formulation provided herein (such as one of those described in Example 6 or Table 2 (e.g., core 1, 2, 3, 4, 5, 6, 7, 8, or 9)).

In some embodiments, the composition comprises a granule and an identifier encapsulated in a capsule. In some embodiments, the composition comprises a plurality of granules.

In some embodiments, the composition comprises:
1) about 92 to about 99.3% w/w of a granule comprising:
  about 10.3% w/w lisinopril;
  about 15.5% w/w dicalcium phosphate;
  about 58.6% w/w mannitol (e.g., 180 μm); and
  about 15.5% w/w pregelatinized starch; and
2) about 0.7 to about 8% w/w of an identifier comprising:
  a) an integrated circuit comprising silicon, aluminum, silicon dioxide, and silicon nitride;
  b) a wafer comprising titanium, titanium-tungsten, gold, magnesium, copper (I) chloride, and hydroxypropyl cellulose; and
  c) a skirt film comprising ethyl cellulose, hydroxypropyl cellulose, and triethyl citrate;
wherein the integrated circuit, wafer and skirt film are coated with a hydroxypropyl cellulose coating, and the granule and identifier are encapsulated within a capsule (e.g., a gelatin or hydroxypropyl methylcellulose capsule).

In some embodiments, the ingestible event marker composition comprises:
1) about 89 to about 98.8% w/w of a granule comprising:
  about 10.3% w/w lisinopril;
  about 15.5% w/w dicalcium phosphate;
  about 58.6% w/w mannitol (e.g., 180 μm);
  about 15.5% w/w pregelatinized starch; and
  about 0.15% w/w iron oxide yellow;
2) about 0.7 to about 8% w/w of an identifier comprising:
  a) an integrated circuit comprising silicon, aluminum, silicon dioxide, and silicon nitride;
  b) a wafer comprising titanium, titanium-tungsten, gold, magnesium, copper (I) chloride, and hydroxypropyl cellulose; and
  c) a skirt film comprising ethyl cellulose, hydroxypropyl cellulose, and triethyl citrate;
3) about 0.5% to about 1% w/w magnesium stearate; and
4) about 0% to about 2% w/w croscarmellose sodium; and
wherein the integrated circuit, wafer and skirt film are coated with a hydroxypropyl cellulose coating, and the granule, identifier magnesium stearate, and croscarmellose sodium are encapsulated within a capsule (e.g., a gelatin or hydroxypropyl methylcellulose capsule).

In some embodiments, the ingestible event marker composition comprises:
1) about 75.5 to about 90.9% w/w of a granule comprising:
  about 10.3% w/w lisinopril;
  about 15.5% w/w dicalcium phosphate;
  about 58.6% w/w mannitol (e.g., 180 μm);
  about 15.5% w/w pregelatinized starch; and
  about 0.15% w/w iron oxide yellow;
2) about 8.6 to about 22% w/w sensor pill comprising:
  a) about 90% w/w microcrystalline cellulose;
  b) about 1.8% w/w croscarmellose sodium;
  c) about 0.5% w/w magnesium stearate; and
  c) about 8% w/w of an identifier comprising:
    a1) an integrated circuit comprising silicon, aluminum, silicon dioxide, and silicon nitride;
    b1) a wafer comprising titanium, titanium-tungsten, gold, magnesium, copper (I) chloride, and hydroxypropyl cellulose; and
    c1) a skirt film comprising ethyl cellulose, hydroxypropyl cellulose, and triethyl citrate;
3) about 0.5 to about 2.5% w/w of an excipient additive comprising:
  about 20% to about 100% w/w magnesium stearate; and
  about 0% to about 80% w/w croscarmellose sodium; and
wherein the integrated circuit, wafer and skirt film are coated with a hydroxypropyl cellulose coating, and the granule, sensor pill, and excipient additive are encapsulated within a capsule (e.g., a gelatin or hydroxypropyl methylcellulose capsule).

In some embodiments, the ingestible event marker composition comprises:
1) about 86.5 to about 93.8% w/w of a granule comprising:
about 10.3% w/w lisinopril;
about 15.5% w/w dicalcium phosphate;
about 58.6% w/w mannitol (e.g., 180 μm);
about 15.5% w/w pregelatinized starch; and
about 0.15% w/w iron oxide yellow;
2) about 0.7 to about 8% w/w of an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
3) about 0.5% w/w magnesium stearate; and
4) about 5% w/w pregelatinized starch; and
wherein the integrated circuit, wafer and skirt film are coated with a hydroxypropyl cellulose coating, and the granule, identifier magnesium stearate, and pregelatinized starch are encapsulated within a capsule (e.g., a gelatin or hydroxypropyl methylcellulose capsule).

In some embodiments, the ingestible event marker composition comprises:
1) about 72.5 to about 85.9% w/w of a granule comprising:
about 10.3% w/w lisinopril;
about 15.5% w/w dicalcium phosphate;
about 58.6% w/w mannitol (e.g., 180 μm);
about 15.5% w/w pregelatinized starch; and
about 0.15% w/w iron oxide yellow;
2) about 8.6 to about 22% w/w sensor pill comprising:
a) about 90% w/w microcrystalline cellulose;
b) about 1.8% w/w croscarmellose sodium;
c) about 0.5% w/w magnesium stearate; and
c) about 8% w/w of an identifier comprising:
a1) an integrated circuit comprising silicon, aluminum, silicon dioxide, and silicon nitride;
b1) a wafer comprising titanium, titanium-tungsten, gold, magnesium, copper (I) chloride, and hydroxypropyl cellulose; and
c1) a skirt film comprising ethyl cellulose, hydroxypropyl cellulose, and triethyl citrate;
3) about 5.5% w/w of an excipient additive comprising:
about 9% w/w magnesium stearate; and
about 910% w/w pregelatinized starch; and
wherein the integrated circuit, wafer and skirt film are coated with a hydroxypropyl cellulose coating, and the granule, identifier, and excipient additive are encapsulated within a capsule (e.g., a gelatin or hydroxypropyl methylcellulose capsule).

In some embodiments, the composition comprises:
1) about 92 to about 99.3% w/w of a granule comprising:
about 11.2% w/w lisinopril;
about 16.9% w/w dicalcium phosphate;
about 60.5% w/w mannitol (e.g., 180 μm); and
about 11.2% w/w pregelatinized starch; and
2) about 0.7 to about 8% w/w of an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
wherein the integrated circuit, wafer and skirt film are coated with a hydroxypropyl cellulose coating, and the granule and identifier are encapsulated within a capsule (e.g., a gelatin or hydroxypropyl methylcellulose capsule).

In some embodiments, the ingestible event marker composition comprises:
1) about 81.5 to about 93.8% w/w of a granule comprising:
about 11.2% w/w lisinopril;
about 16.9% w/w dicalcium phosphate;
about 60.5% w/w mannitol (e.g., 180 μm);
about 11.2% w/w pregelatinized starch; and
about 0.15% w/w iron oxide yellow; and
2) about 0.7 to about 8% w/w of an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
3) about 0.5% w/w magnesium stearate; and
4) about 5 to about 10% w/w pregelatinized starch; and
wherein the integrated circuit, wafer and skirt film are coated with a hydroxypropyl cellulose coating, and the granule, identifier, magnesium stearate, and pregelatinized starch are encapsulated within a capsule (e.g., a gelatin or hydroxypropyl methylcellulose capsule).

In some embodiments, the ingestible event marker composition comprises:
1) about 67.5 to about 85.9% w/w of a granule comprising:
about 11.2% w/w lisinopril;
about 16.9% w/w dicalcium phosphate;
about 60.5% w/w mannitol (e.g., 180 μm);
about 11.2% w/w pregelatinized starch; and
about 0.15% w/w iron oxide yellow; and
2) about 8.6 to about 22% w/w of a sensor pill comprising:
a) about 90% w/w microcrystalline cellulose;
b) about 1.8% w/w croscarmellose sodium;
c) about 0.5% w/w magnesium stearate; and
c) about 8% w/w of an identifier comprising:
a1) an integrated circuit comprising silicon, aluminum, silicon dioxide, and silicon nitride;
b1) a wafer comprising titanium, titanium-tungsten, gold, magnesium, copper (I) chloride, and hydroxypropyl cellulose; and
c1) a skirt film comprising ethyl cellulose, hydroxypropyl cellulose, and triethyl citrate;
3) about 5.5 to about 10.5% w/w of an excipient additive comprising:
about 5 to about 9% w/w magnesium stearate; and
about 910% to about 95% w/w pregelatinized starch; and
wherein the integrated circuit, wafer and skirt film are coated with a hydroxypropyl cellulose coating, and the granule, sensor pill, and excipient additive are encapsulated within a capsule (e.g., a gelatin or hydroxypropyl methylcellulose capsule).

In some embodiments, the ingestible event marker composition comprises:
1) about 86.5 to about 93.8% w/w of a granule comprising:
about 11.2% w/w lisinopril;
about 16.9% w/w dicalcium phosphate;
about 60.5% w/w mannitol (e.g., 180 μm);
about 11.2% w/w pregelatinized starch; and
about 0.15% w/w iron oxide yellow; and 2) about 0.7 to about 8% w/w of an identifier comprising:
  a) an integrated circuit comprising silicon, aluminum, silicon dioxide, and silicon nitride;
  b) a wafer comprising titanium, titanium-tungsten, gold, magnesium, copper (I) chloride, and hydroxypropyl cellulose; and
  c) a skirt film comprising ethyl cellulose, hydroxypropyl cellulose, and triethyl citrate;
3) about 0.5% w/w magnesium stearate; and
4) about 5% w/w pregelatinized starch; and
wherein the integrated circuit, wafer and skirt film are coated with a hydroxypropyl cellulose coating, and the granule, identifier, magnesium stearate, and pregelatinized starch are encapsulated within a capsule (e.g., a gelatin or hydroxypropyl methylcellulose capsule).

In some embodiments, the ingestible event marker composition comprises:
1) about 72.5 to about 85.9% w/w of a granule comprising:
  about 11.2% w/w lisinopril;
  about 16.9% w/w dicalcium phosphate;
  about 60.5% w/w mannitol (e.g., 180 µm);
  about 11.2% w/w pregelatinized starch; and
  about 0.15% w/w iron oxide yellow; and
2) about 8.6 to about 22% w/w of a sensor pill comprising:
  a) about 90% w/w microcrystalline cellulose;
  b) about 1.8% w/w croscarmellose sodium;
  c) about 0.5% w/w magnesium stearate; and
  c) about 8% w/w of an identifier comprising:
    a1) an integrated circuit comprising silicon, aluminum, silicon dioxide, and silicon nitride;
    b1) a wafer comprising titanium, titanium-tungsten, gold, magnesium, copper (I) chloride, and hydroxypropyl cellulose; and
    c1) a skirt film comprising ethyl cellulose, hydroxypropyl cellulose, and triethyl citrate;
3) about 5.5% w/w of an excipient additive comprising:
  about 9% w/w magnesium stearate; and
  about 910% w/w pregelatinized starch; and
wherein the integrated circuit, wafer and skirt film are coated with a hydroxypropyl cellulose coating, and the granule, sensor pill, and excipient additive are encapsulated within a capsule (e.g., a gelatin or hydroxypropyl methylcellulose capsule).

In some embodiments, the composition is in a compressed tablet form. In some embodiments, the compressed tablet comprises an inner compressed tablet encapsulated (e.g. dry coated or mantle coated) within an outer compressed shell.

In some embodiments, the ingestible event marker composition comprises:
  about 7.3% w/w lisinopril;
  about 30.0% w/w dicalcium phosphate dihydrate (di-tab);
  about 24.6% w/w mannitol (e.g., 50 µm);
  about 20.0% w/w pregelatinized starch;
  about 15.0% w/w microcrystalline cellulose;
  about 2.0% w/w croscarmellose sodium;
  about 0.15% w/w yellow iron oxide;
  about 1.0% w/w magnesium stearate; and
  an identifier comprising:
    a) an integrated circuit comprising silicon, aluminum, silicon dioxide, and silicon nitride;
    b) a wafer comprising titanium, titanium-tungsten, gold, magnesium, copper (I) chloride, and hydroxypropyl cellulose; and
    c) a skirt film comprising ethyl cellulose, hydroxypropyl cellulose, and triethyl citrate;
  wherein the integrated circuit, wafer and skirt film are coated with a hydroxypropyl cellulose coating.

In some embodiments, the ingestible event marker composition comprises:
  about 7.3% w/w lisinopril;
  about 15.0% w/w dicalcium phosphate dihydrate (di-tab);
  about 24.6% w/w mannitol (e.g., 50 µm);
  about 20.0% w/w pregelatinized starch;
  about 30.0% w/w microcrystalline cellulose;
  about 2.0% w/w croscarmellose sodium;
  about 0.15% w/w yellow iron oxide;
  about 1.0% w/w magnesium stearate; and
  an identifier comprising:
    a) an integrated circuit comprising silicon, aluminum, silicon dioxide, and silicon nitride;
    b) a wafer comprising titanium, titanium-tungsten, gold, magnesium, copper (I) chloride, and hydroxypropyl cellulose; and
    c) a skirt film comprising ethyl cellulose, hydroxypropyl cellulose, and triethyl citrate;
  wherein the integrated circuit, wafer and skirt film are coated with a hydroxypropyl cellulose coating.

In some embodiments, the ingestible event marker composition comprises:
  about 7.3% w/w lisinopril;
  about 30.0% w/w dicalcium phosphate dihydrate (di-tab);
  about 24.6% w/w mannitol (e.g., 50 µm);
  about 20.0% w/w pregelatinized starch;
  about 15.0% w/w microcrystalline cellulose;
  about 2.0% w/w croscarmellose sodium;
  about 0.15% w/w yellow iron oxide;
  about 1.0% w/w magnesium stearate; and
  an identifier comprising:
    a) an integrated circuit comprising silicon, aluminum, silicon dioxide, and silicon nitride;
    b) a wafer comprising titanium, titanium-tungsten, gold, magnesium, copper (I) chloride, and hydroxypropyl cellulose; and
    c) a skirt film comprising ethyl cellulose, hydroxypropyl cellulose, and triethyl citrate;
  wherein
  the integrated circuit, wafer and skirt film are coated with a hydroxypropyl cellulose coating,
  the lisinopril, dicalcium phosphate dihydrate, mannitol (e.g., 50 µm), pregelatinized starch, microcrystalline cellulose, croscarmellose sodium, yellow iron oxide, and identifier are compressed to form an inner compressed tablet, and
  the magnesium stearate is compressed as an outer compressed shell encapsulating the inner compressed tablet.

In some embodiments, the ingestible event marker composition comprises:
  about 7.3% w/w lisinopril;
  about 15.0% w/w dicalcium phosphate dihydrate (di-tab);
  about 24.6% w/w mannitol (e.g., 50 µm);
  about 20.0% w/w pregelatinized starch;
  about 30.0% w/w microcrystalline cellulose;
  about 2.0% w/w croscarmellose sodium;
  about 0.15% w/w yellow iron oxide;
  about 1.0% w/w magnesium stearate; and
  an identifier comprising:
    a) an integrated circuit comprising silicon, aluminum, silicon dioxide, and silicon nitride;
    b) a wafer comprising titanium, titanium-tungsten, gold, magnesium, copper (I) chloride, and hydroxypropyl cellulose; and
    c) a skirt film comprising ethyl cellulose, hydroxypropyl cellulose, and triethyl citrate;

wherein the integrated circuit, wafer and skirt film are coated with a hydroxypropyl cellulose coating, the lisinopril, dicalcium phosphate dihydrate, mannitol (e.g., 50 µm), pregelatinized starch, microcrystalline cellulose, croscarmellose sodium, yellow iron oxide, and identifier are compressed to form an inner compressed tablet, and the magnesium stearate is compressed as an outer compressed shell encapsulating the inner compressed tablet.

Identifiers

Also present in the subject compositions is an identifier. The identifier may vary depending on the particular embodiment and intended application of the composition. In certain embodiments, the identifier may be a component that emits a signal upon activation by a stimulus, e.g., by interrogation, upon contact with a target physiological location, etc. As such, the identifier may be an identifier that emits a signal when it contacts a target body (i.e., physiological) site. In addition or alternatively, the identifier may be an identifier that emits a signal when interrogated.

In yet other embodiments, the identifier may be an inert, but identifiable marker, e.g., an engraved identifier (such as one that is fabricated from a material or materials that survive digestion). This marker may then be identified, for example, following an autopsy or forensic examination. It is possible to provide a more internal device within a pill to determine both that its surface has partially been subject to digestion, but also that the inner pill material has also been digested. This application may be particularly useful in experimental pharmacological settings. The identifier of these embodiments may be one that does not necessarily emit a signal, but which can be optically inspected, e.g., visually or machine read, to obtain information about the composition with which it was associated prior to administration.

While the identifier may be an identifier that does not emit a signal, in certain embodiments, as summarized above, the identifier may be one that does emit a signal. Depending on the needs of a particular application, the signal may be a generic signal, e.g., a signal that merely identifies that the composition has contacted the target site, or a unique signal, e.g., a signal which in some way uniquely identifies that a particular composition from a group or plurality of different compositions in a batch has contacted a target physiological site. As such, the identifier may be one that, when employed in a batch of unit dosages, e.g., a batch of tablets, may emit a signal which cannot be distinguished from the signal emitted by the identifier of any other unit dosage member of the batch. In yet other embodiments, the identifier may emit a signal that uniquely identifies a given unit dosage, even from other identical unit dosages in a given batch. Accordingly, in certain embodiments, the identifier may emit a unique signal that distinguishes a given type of unit dosage from other types of unit dosages, e.g., a given medication from other types of medications. In certain embodiments, the identifier may emit a unique signal that distinguishes a given unit dosage from other unit dosages of a defined population of unit dosages, e.g., a prescription, a batch or a lifetime production run of dosage formulations. In certain embodiments, the identifier may emit a signal that is unique, i.e., distinguishable, from a signal emitted by any other dosage formulation ever produced, where such a signal may be viewed as a universally unique signal (e.g., analogous to a human fingerprint which is distinct from any other fingerprint of any other individual and therefore uniquely identifies an individual on a universal level). In one embodiment, the signal may either directly convey information about the composition, or provide an identifying code, which may be used to retrieve information about the composition from a database, i.e., a database linking identifying codes with compositions.

The identifier may be any component or device that is capable of generating a detectable signal following activation in response to a stimulus. In certain embodiments, the stimulus may activate the identifier to emit a signal once the composition comes into contact with a physiological target site, e.g., as summarized above. For example, a patient may ingest a pill that upon contact with the stomach fluids, generates a detectable signal. Depending on the embodiment, the target physiological site or location may vary, where representative target physiological sites of interest include, but are not limited to: a location in the gastrointestinal tract (such as the mouth, esophagus, stomach, small intestine, large intestine, etc.); another location inside the body, such as a parental location, vascular location, etc.; or a topical location; etc.

In certain embodiments, the stimulus that activates the identifier may be an interrogation signal, such as a scan or other type of interrogation. In these embodiments, the stimulus may activate the identifier, thereby emitting a signal which may then be received and processed, e.g., to identify the composition in some manner.

In certain of these embodiments, the identifier may include a power source that transduces broadcast power and a signal generating element that modulates the amount of transduced power, such that a signal is not emitted from the identifier but instead the amount of broadcast power transduced by the identifier is detected and employed as the "signal." Such embodiments may be useful in a variety of applications, such as applications where the history of a given composition may be of interest, e.g., as reviewed in greater detail below.

In certain embodiments, the identifier may be dimensioned to be complexed with the lisinopril/pharmaceutically acceptable carrier component to produce a composition that can be readily administered to a subject in need thereof. As such, in certain embodiments, the identifier element may be dimensioned to have a width ranging from about 0.05 mm to about 1 mm, such as from about 0.1 mm to about 0.2 mm; a length ranging from about 0.05 mm to about 1 mm, such as from about 0.1 mm to about 0.2 mm and a height ranging from about 0.1 mm to about 1 mm, such as from about 0.05 mm to about 0.3 mm, including from about 0.1 mm to about 0.2 mm. In certain embodiments, the identifier may be 1 mm$^3$ or smaller, such as 0.1 mm$^3$ or smaller, including 0.2 mm$^3$ or smaller. The identifier element may take a variety of different configurations, such as but not limited to: a chip configuration, a cylinder configuration, a spherical configuration, a disc configuration, etc., where a particular configuration may be selected based on intended application, method of manufacture, etc.

The identifier may generate a variety of different types of signals, including but not limited to, RF, magnetic, conductive (near field), acoustic, etc.

In certain embodiments, the identifier may be one that is programmable following manufacture, in the sense that the signal generated by the identifier may be determined after the identifier is produced, where the identifier may be field programmable, mass programmable, fuse programmable, and even reprogrammable. Such embodiments are of interest where uncoded identifiers are first produced and following incorporation into a composition are then coded to emit an identifying signal for that composition. Any convenient programming technology may be employed. In certain embodiments, the programming technology employed is RFID technology. RFID smart tag technology of interest that may be employed in the subject identifiers includes, but is not limited to: that described in U.S. Pat. Nos. 7,035,877; 7,035,818; 7,032,822; 7,031,946, as well as published application no. US20050131281, and the like, the disclosures of which are herein incorporated by reference. With RFID or other smart tag technology, a manufacturer/vendor may associate a unique ID code with a given identifier, even after the identifier has been incorporated into the composition. In certain embodiments, each individual or entity involved in the handling of the composition prior to use may introduce information into the identifier, e.g., in the form of programming with respect to the signal emitted by the identifier, e.g., as described in U.S. Pat. No. 7,031,946 the disclosure of which is herein incorporated by reference.

The identifier of certain embodiments may include a memory element, where the memory element may vary with respect to its capacity. In certain embodiments, the memory element may have a capacity ranging from about 1 bit to 1 gigabyte or more, such as 1 bit to 1 megabyte, including from about 1 bit to about 128 bit. The particular capacity employed may vary depending on the application, e.g., whether the signal is a generic signal or coded signal, and where the signal may or may not be annotated with some additional information, e.g., name of lisinopril, etc.

Identifier components of embodiments of the disclosure may have: (a) an activation component and (b) a signal generation component, where the signal generation component is activated by the activation component to produce an identifying signal, e.g., as described above.

Activation Component

The activation component may be a component that activates the signal generation element to emit a signal upon experience of a stimulus, e.g., contact of the composition with a target physiological site of interest, such as the stomach. The activation component may be integrated with a power source, e.g., a battery. Illustrative activation approaches may include, but are not limited to: Battery Completion, e.g., Battery activated by electrolyte addition and Battery activated by cathode or anode addition; Battery connection, e.g., Battery activated by conductor addition; Transistor-mediated Battery Connection, e.g., Battery activated by transistor gate, Geometry Modification, Detection of Geometry Modification by Resonant Structure, Pressure Detection, Resonant Structure Modification; etc.

Battery/Power Source

In certain embodiments, the power source may be turned on upon contact of the power source with a target site, e.g., a physiological target site, such as the stomach, e.g., stomach acid. In certain embodiments, the power source may be a battery that is turned on to provide power upon contact with the physiological target site, where the battery is coupled to the signal generation component such that when the battery is turned on, the signal generation component may emit the identifying signal.

In certain embodiments, the battery that is employed may be one that comprises the two dissimilar materials magnesium metal and copper chloride (e.g., copper (I) chloride, CuCl, or cuprous chloride), which constitute the two electrodes of the battery. In certain embodiments, these two materials may be shielded from the surrounding environment by an additional layer of material. When the shielding material (e.g., lisinopril/carrier matrix), is dissolved or eroded by the surrounding fluid, the electrode materials may be exposed and come in contact with the body fluid, such as stomach acid or other types of electrolyte fluid. A potential difference, that is, a voltage, may be generated between the electrodes as a result of the respective oxidation and reduction reactions incurred to the two electrode materials. A voltaic cell, or battery, can be thereby formed. Accordingly, in some embodiments of the disclosure, such batteries may be configured such that when the two dissimilar materials are exposed to the target site, e.g., the stomach, the digestive tract, etc., during the physical and chemical erosion of the composition in which the signal generation element is present, a voltage may be generated. In such embodiments, the power source described above is not a "battery" in the common sense of the word, but rather as defined in the discipline of physics. The two dissimilar materials (magnesium metal and copper chloride) in an electrolyte may be at different potentials. As a result, a potential difference between the two dissimilar materials may be generated.

Various battery-activation configurations are possible. Representative types of cell-activation approaches may include, but are not limited to: activation by presence of electrolyte, activation by presence of a cathode material, activation by presence of a conductive material.

After the battery is activated, further activation configurations can be employed to activate the signal generation component. For example, the signal generation component can be activated through the activation of the gate of a metal oxide semiconductor (MOS) circuit, such as a CMOS switch. Activation of the gate of the MOS circuit can be based on one or more parameters, which may include but are not limited to: gate current, gate charge, and gate capacitance.

The gate current, for activation purposes, can be a function of the conductivity of surrounding body fluids or tissues. Such conductivity can further be a function of one or more parameters, which may include but are not limited to: solution concentration, solution pH value, ionic content of solution, enzymatic content of solution, temperature, and carrier mobility. Carrier mobility can also be a function of temperature.

Similarly, the gate charge can be a function of one or more parameters, which may include but are not limited to: solution composition, crystal potential, electrical potential, gravitational potential, gate capacitance, and carrier concentration. The carrier concentration can also be a function of temperature.

The gate capacitance can be a function of the capacitive geometry of the gate, which can further be a function of pressure, a resonant input, or the characteristics of a dielectric material coupled to the gate. The characteristics of the dielectric material can vary with one or more parameters, which may include but are not limited to: chemical contents of a digestive tract, chemical character of a physiological location, and amount of dissolution of the dielectric material in body fluids.

In certain embodiments, the battery may be one that is made up of active electrode materials, electrolyte, and inactive materials, such as current collectors, packaging, etc. The active materials are a pair made up of magnesium metal and copper chloride.

The electrode materials provided herein are copper chloride (e.g., copper (I) chloride, CuCl, or cuprous chloride) as the cathode and magnesium metal as the anode.

Some embodiments of the batteries described herein provide for a voltage upon contact with the target physiological site, e.g., the stomach, sufficient to drive the signal generation element of the identifier. In certain embodiments, the voltage provided by the electrode materials upon contact of the metals of the power source with the target physiological site may be 0.001 V or higher, including 0.01 V or higher, such as 0.1 V or higher, e.g., 0.3 V or higher, including 0.5 volts or higher, and including 1.0 volts or higher, where in certain embodiments, the voltage may range from about 0.001 to about 10 volts, such as from about 0.01 to about 10 V.

In certain embodiments, the batteries may have a small form factor. Batteries may be 10 mm$^3$ or smaller, such as 1.0 mm$^3$ or smaller, including 0.1 mm$^3$ or smaller, including 0.02 mm$^3$ or smaller. As such, in certain embodiments, the battery element is dimensioned to have a width ranging from about 0.05 mm to about 1 mm, such as from about 0.1 mm to about 0.2 mm; a length ranging from about 0.05 mm to about 1 mm, such as from about 0.1 mm to about 0.2 mm and a height ranging from about 0.1 mm to about 1 mm, such as from about 0.05 mm to about 0.3 mm, including from about 0.1 mm to about 0.2 mm.

In certain embodiments, the battery may have a split or segmented configuration.

In certain embodiments, the battery may be one free of packaging. As such, the electrodes may be exposed and not protected by any protecting or sealing structure. As such, following removal of the lisinopril/carrier matrix material with which the battery may be associated, the battery per se does not itself include a protective packaging such that the electrodes may be free to contact the electrolyte at the target physiological location.

In certain embodiments, the battery power source may be viewed as a power source that exploits reverse electrolysis in an ionic solution such as gastric fluid, blood, or other bodily fluids and some tissues.

Where the power source is a battery, the battery may be fabricated in a number of different ways. In certain embodiments, fabrication protocols which may be categorized as "planar" processing protocols are employed, as developed in greater detail below.

Signal Generation Component

The signal generation component of the identifier element is a structure that, upon activation by the activation component, may emit a detectable signal, e.g., that can be received by a receiver. The signal generation component of certain embodiments can be any convenient device that is capable of producing a detectable signal and/or modulating transduced broadcast power, upon activation by the activation component. Detectable signals of interest include, but are not limited to: conductive signals, acoustic signals, etc. As reviewed above, the signals emitted by the signal generator may be generic or unique signals, where representative types of signals of interest include, but are not limited to: frequency shift coded signals; amplitude modulation signals; frequency modulation signals; etc.

In certain embodiments, the signal generation element may include circuitry which produces or generates the signal. The type of circuitry chosen may depend, at least in part, on the driving power that is supplied by the power source of the identifier. For example, where the driving power is 1.2 volts or above, standard CMOS circuitry may be employed. In other embodiments where the driving power ranges from about 0.7 to about 1.2 V, sub-threshold circuit designs may be employed. For driving powers of about 0.7 V or less, zero-threshold transistor designs may be employed.

In certain embodiments, the signal generation component includes a voltage-controlled oscillator (VCO) that can generate a digital clock signal in response to activation by the activation component. The VCO can be controlled by a digital circuit, which is assigned an address and which can control the VCO with a control voltage. This digital control circuit can be embedded onto a chip that includes the activation component and oscillator. Using phase shift keying to encode the address, an identifying signal can be transmitted.

The signal generation component may include a distinct transmitter component that serves to transmit the generated signal to a remote receiver, which may be internal or external to the patient, as reviewed in greater detail below. The transmitter component, when present, may take a number of different configurations, e.g., depending on the type of signal that is generated and is to be emitted. In certain embodiments, the transmitter component may be made up of one or more electrodes. In certain embodiments, the transmitter component may be made up of one or more wires, e.g., in the form of antenna(e). In certain embodiments, the transmitter component may be made up of one or more coils. As such, the signal transmitter may include a variety of different transmitters, e.g., electrodes, antennas (e.g., in the form of wires) coils, etc. In certain embodiments, the signal may be transmitted either by one or two electrodes or by one or two wires. A two-electrode transmitter may be a dipole; a one electrode transmitter forms a monopole. In certain embodiments, the transmitter may only require one diode drop of power.

Additional Components

Depending on the particular embodiment, the identifier may include a number of different additional components. Some components of interest include, but are not limited, those reviewed below.

Power Enhancers

Where the activator is a power source that is turned on upon contact with a target physiological site, in certain embodiments, circuits for enhancing or boosting voltage of the analog circuit voltage rails, may be provided, e.g., charge pumping circuits, charge doublers, etc. By increasing the voltage of certain nodes, improved performance of critical functions, such as oscillators, can be achieved.

Power Storage

In certain embodiments, the activation component may include a power storage element. For example, a duty cycle configuration may be employed, e.g., where slow energy production from a battery is stored in a power storage element, e.g., in a capacitor, which then may provide a burst of power that may be deployed to the signal generation component. In certain embodiments, the activation component may include a timing element which modulates, e.g., delays, delivery of power to the signal generation element, e.g., so signals from different compositions, e.g., pills, that are administered at substantially the same time may be produced at different times and are therefore distinguishable.

Identifier Fabrication

In certain embodiments of interest, the identifier element includes a semiconductor support component. Any of a variety of different protocols may be employed in manufacturing the identifier structures and components thereof. For example, molding, deposition and material removal, e.g., planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electroplating, cathodic arc deposition, plasma spray, sputtering, e-beam evaporation, physical vapor deposition, chemical vapor deposition, plasma enhanced chemical vapor deposition, etc. Material removal techniques include, but are not limited to:

reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner.

Specific Pill Embodiments

In further describing various embodiments of the compositions of the disclosure, specific embodiments are now described in greater detail in view of the figures. In the following detailed description, reference is made to the accompanying drawings, which form a part hereof. In the drawings, similar symbols and reference characters typically identify similar components throughout the several views, unless context dictates otherwise.

FIG. 1 is a diagrammatic, exemplary representation of a pill/capsule embodiment of the present disclosure, according to one aspect of the present disclosure, in which the composition is configured as an orally ingestible pharmaceutical formulation in the form of a pill or capsule. The stomach 12 of the patient 10 who ingests the composition 14 is shown. This "smart pill" is shown as it has traveled from the mouth 16 to inside 18 the patient's stomach. Upon reaching the stomach, the pill/capsule may undergo a dissolving process with both the mechanical action of the stomach and the various chemical materials in the stomach fluids, such as hydrochloric acid and other digestive agents.

Figure 2:
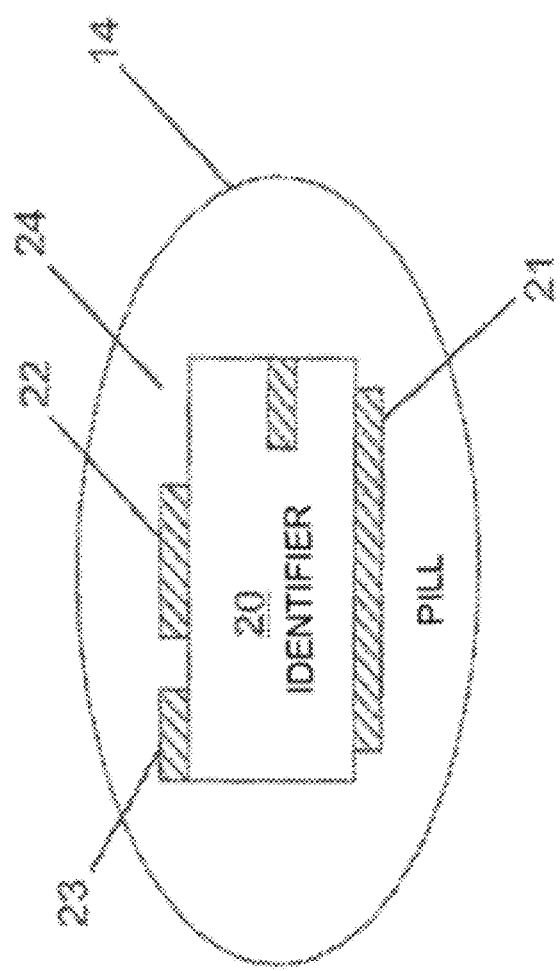
FIG. 2 is a more detailed view of the pill composition shown in FIG. 1, according to one aspect of the present disclosure.

FIG. 2 is a more detailed view of the pill composition shown in FIG. 1. FIG. 2 illustrates an identifier 20 disposed inside a pill 14. Identifier 20 is present as an integrated circuit (IC). The backside (bottom) of circuit 20 may be at least partially coated with a first metal 21, and a portion of the front (top) of circuit 20 may be coated with a different metal 22, allowing circuit 20 to be powered by reverse electrolysis. Also on the top surface may be two transmitter electrodes 23, 24.

When pill 14 is fabricated, the integrated circuit 20 may be surrounded by at least one external layer that may include pharmacologically active and/or inert materials in any combination. The external layer may dissolve in the stomach through a combination of the mechanical action of the stomach and the action of various chemical constituents (e.g., hydrochloric acid) in stomach fluids.

As pill 14 is dissolved, areas of integrated circuit 20 may become exposed to the stomach contents, which for present purposes can be regarded as an electrolyte solution. As dissolution of the pill exposes metal layers 21 and 22 (magnesium metal and copper chloride), power may be supplied to circuit 20, which may begin to operate and continue to operate until metal layers 21 and 22 or the circuit itself are sufficiently dissolved by digestive processes and acids to become non-functional. Eventually, the remains of the chip are excreted from the body.

In an alternative embodiment, the integrated circuit 20 may be attached to, rather than encapsulated in, the pill 14. For instance, circuit 20 might be placed at one end of the pill as the pill is being prepared, in a soluble coating on the surface of the pill, or the like. In embodiments where circuit 20 is wholly or partially exposed, integrated circuit 20 may begin to operate sooner after the pill enters the stomach rather than after the pill dissolves.

In one embodiment, circuit 20 may transmit a signal identifying pill 14. The identifier may indicate the type (lisinopril, brand, etc.) and/or dosage of pill 14 and may also provide a lot number, serial number, or similar identifying information that would allow particular pills to be traced, e.g., as reviewed above.

Figure 3:
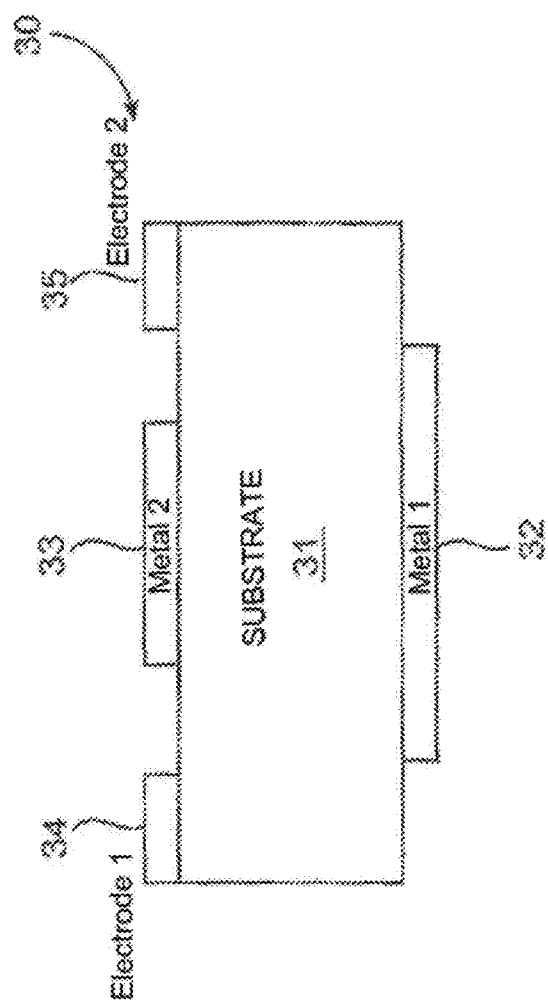
FIG. 3 is an example embodiment of signal generation elements of the pill composition shown in FIG. 1, according to one aspect of the present disclosure.

FIG. 3 is a detailed depiction of an embodiment of a signal generation element 30 which labels the pharmaceutical material and is encapsulated in the center of the composition, according to one aspect of the present disclosure. Signal generation element 30 is in the form of IC constructed from a silicon chip where various functional elements, e.g., in the form of one or more layers of circuits, may be disposed on a silicon substrate 31. The chip can be fabricated using standard integrated circuit techniques. An example of such a fabrication approach may be a 0.5μ CMOS process made available by AMI Semiconductor in Idaho, USA. Shown on the backside of the substrate, the bottom of the chip 31 may be metal 1 32 which functions as one battery electrode (magnesium metal or copper chloride), and on the topside of the chip may be metal 2 33 which functions as the other battery electrode (copper chloride, or magnesium metal). Also on the top side of the chip 31 may be electrode 1 34 and electrode 2 35, which may constitute a pair of signal-transmission electrodes.

In some cases, dissolution of the electrodes, and thus extinction of the reporting signal, can provide a secondary indication of the full dissolution of the pill and incorporated devices.

A potential applied to the silicon may be a positive voltage on the top surface and a negative voltage on the bottom surface. In this way, the substrate may be essentially at the same potential as the cathode, which can be the ground reference for the circuits, and the top surface, with a $SiO_2$ insulation layer, may be coupled to a positive voltage, referenced to that ground on the bottom side.

Figure 4A:
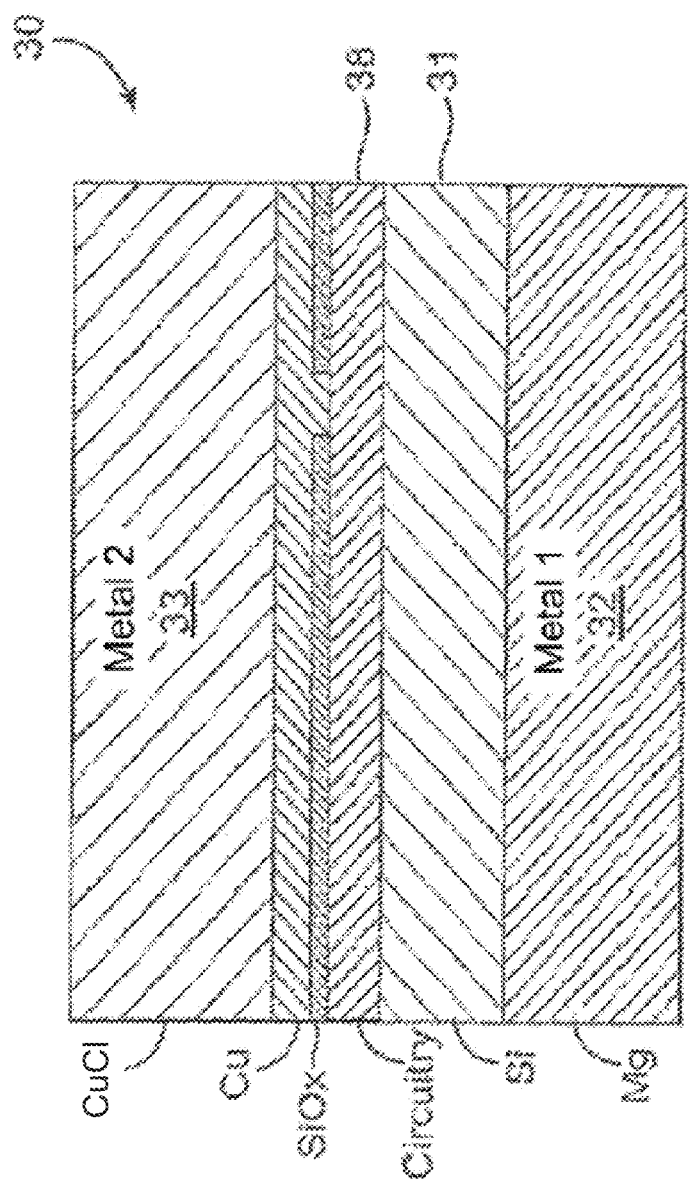
FIGS. 4A and 4B are example embodiments of signal generation elements of the pill composition shown in FIG. 1, according to some aspects of the present disclosures.
Figure 4B:
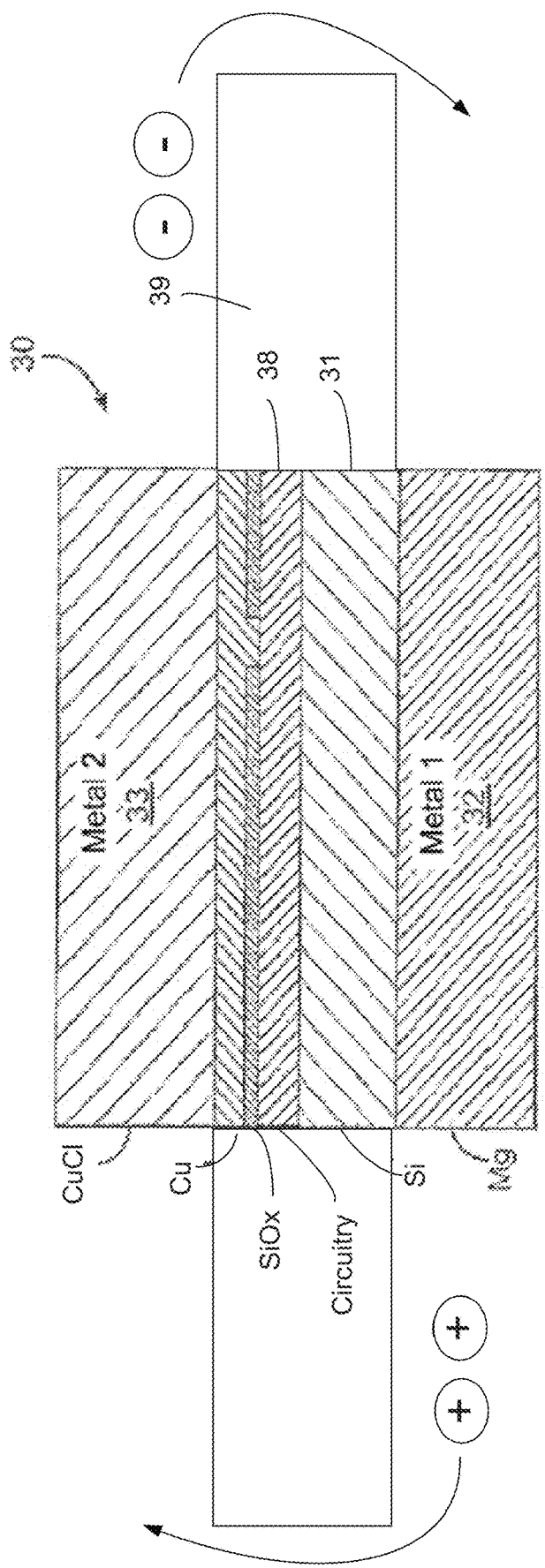

In certain embodiments, the signal generation element may not include antennae and instead uses battery components as antennae, such as shown in FIGS. 4A and 4B. In FIG. 4A, signal generation element 30 may include silicon support layer 31 positioned between metal 1 layer 32 and metal 2 layer 33. Also shown is circuitry layer 38. In such embodiments, when a switch on the chip, e.g., in the circuitry layer, is closed, a current may be produced between the two metals of the battery, which is then detected. In certain embodiments, a membrane larger than the chip, which defines a path for the current to travel, may be provided. As shown in FIG. 4B, in certain embodiments, a non-conductive "skirt" membrane or film 39 is attached to the chip that increases the length of the conductive current path between metal 1 layer 32 and metal 2 layer 33. As illustrated, the positive and negative ions must travel around the non-conductive skirt membrane or film 39, increasing the current path. The dipole moment is therefore increased, which increases signal strength generated by the chip powered by the closed circuit formed by the current path between the metal 1 layer 32 and the metal 2 layer 33. The non-conductive skirt membrane or film 39 may be composed of non-conductive material, such as hydroxypropyl cellulose, or other compositions of cellulose described herein.

Methods of Making Compositions

The compositions provided herein address a number of intertwined problems related to development of functional lisinopril/IEM compositions such as, but not limited to, those related to the specific active pharmaceutical ingredient used herein (e.g., long disintegration times, or slow dissolution times), functionality of the IEM (e.g., long time to activation, low peak mean amplitude of signal, die fall out, mechanical stability of the compositions (e.g., tablet cracking, or poor friability), and shelf-life stability of the active pharmaceutical ingredient, tablet, or IEM. For example, one should not expect that certain carriers described herein are readily interchangeable with other pharmaceutically acceptable carriers while also addressing, at least, each of the above-noted issues. Similarly, one should not expect that certain IEM elements described herein are readily interchangeable with others while also addressing, at least, each of the above-noted issues. Furthermore, one should not expect that the specific active pharmaceutical ingredient (i.e., lisinopril) described herein is readily interchangeable with other active pharmaceutical ingredients while also addressing, at least, each of the above-noted issues.

A variety of manufacturing protocols may be employed to produce compositions according to the present disclosure. In manufacturing the subject compositions, a signal generation element may be stably associated with the pharmaceutical dosage such that the signal generation element and the dosage do not separate from each other, at least until administered to the subject in need thereof, e.g., by ingestion. The signal generation element may be stably associated with the pharmaceutical carrier/lisinopril component of the composition in a number of different ways.

In some embodiments, where the carrier/lisinopril component is a solid structure, e.g., such as a tablet or pill, the carrier/lisinopril component may be produced in a manner that provides a cavity for the signal generation element. The signal generation element may then be placed into the cavity and the cavity sealed, e.g., with a biocompatible material, to produce the final composition. For example, in certain embodiments, a tablet may be produced with a die that includes a feature which produces a cavity in the resultant compressed tablet. The signal generation element may be placed into the cavity and the cavity sealed to produce the final tablet. In a variation of this embodiment, the tablet may be compressed with a removable element, e.g., in the shape of a rod or other convenient shape. The removable element may then be removed to produce a cavity in the tablet. The signal generation element may be placed into the cavity and the cavity sealed to produce the final tablet. In another variation of this embodiment, a tablet without any cavity is first produced and then a cavity is produced in the tablet, e.g., by laser drilling. The signal generation element is placed into the cavity and the cavity sealed to produce the final tablet.

In some embodiments, a tablet may be produced by combining the signal generation element with subparts of the tablet, where the subparts may be pre-made subparts or manufactured sequentially. For example, in certain embodiments tablets may be produced by first making a bottom half of the tablet, placing the signal generation element on a location of the bottom half of the tablet, and then placing top portion of the tablet over the bottom half and signal generation element to produce the final desired composition.

In some embodiments, a tablet may be produced around a signal generation element such that the signal generation element is located inside of the produced tablet. For example, a signal generation element, which may or may not be encapsulated in a biocompatible compliant material, e.g., gelatin (to protect the signal generation element), may be combined with carrier/lisinopril precursor, e.g., powder, and compressed or molded into a tablet in a manner such that the signal generation element is located at an internal position of the tablet.

The inventors have recognized that it is difficult to combine a pharmaceutical compound with an IEM device to manufacture a stable pharmaceutical product with a reasonable shelf life that meets the FDA requirements and still achieve the functions of the IEM device. For example, tablets may be manufactured by pressing the pharmaceutical compound with a certain pressure, but when an IEM device is combined with the pharmaceutical compound to make the tablets, the pressure used to press the tablets must be carefully tested. Too much pressure would likely damage the IEM device, but if too little pressure is used, the manufactured tablets may not have the desired hardness and other properties to meet the FDA requirements. Further, the conditions of the manufacturing process may vary depending on the specific compositions used, such as the lisinopril, the elements/compositions of the IEM device, and the amounts thereof, which may also affect the properties of the manufactured pharmaceutical product, such as tablets. The inventors have surprisingly discovered that the compositions of the present disclosure, for example, when manufactured as described in greater detail below, may meet the desired requirements while still achieving the desired functions of the IEM device.

Accordingly, the present disclosure provides a unique composition of matter comprising the combination of the IEM electronic circuitry comprising battery forming materials and specific formulations of lisinopril to confirm the delivery of the specific formulations of lisinopril. The compositions provided herein overcome the unpredictable nature (e.g., impact on functionality, shelf-life, structural stability, chemical stability, etc.) of combining various metals and salts with the specific formulations of lisinopril to provide an electronic IEM delivery system that generates its own electrical power from a partial energy source comprised of dissimilar materials when exposed with the bodily fluids of a patient during the oral administration of the specific formulations of lisinopril.

Methods of Treatment

In one aspect, provided herein are methods of treating a disease in a subject in need thereof, comprising administering a lisinopril composition provided herein to the subject. In some embodiments, the disease is hypertension, congestive heart failure, acute myocardial infarction, or diabetic nephropathy. Thus, in some embodiments, provided herein is a method of treating hypertension in a subject in need thereof, comprising administering a lisinopril composition provided herein to the subject. In some embodiments, provided herein is a method of treating congestive heart failure in a subject in need thereof, comprising administering a lisinopril composition provided herein to the subject. In some embodiments, provided herein is a method of treating acute myocardial infarction in a subject in need thereof, comprising administering a lisinopril composition provided herein to the subject. In some embodiments, provided herein is a method of treating diabetic nephropathy in a subject in need thereof, comprising administering a lisinopril composition provided herein to the subject.

In some embodiments, provided herein is a method of treating a disease (e.g., hypertension, congestive heart failure, acute myocardial infarction, or diabetic nephropathy) in a subject in need thereof comprising administering an ingestible event marker composition to the subject, wherein the composition comprises:

1) a granule comprising:
about 10.3% w/w lisinopril;
about 15.5% w/w dicalcium phosphate dihydrate;
about 58.6% w/w mannitol (e.g., 180 μm);

about 15.5% w/w pregelatinized starch; and
about 0.15% w/w iron oxide yellow;
2) an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
3) about 0.5% to about 1% w/w magnesium stearate; and
4) about 0% to about 2% w/w croscarmellose sodium; and
wherein the integrated circuit, wafer and skirt film are coated with a hydroxypropyl cellulose coating, and the granule, identifier magnesium stearate, and croscarmellose sodium are encapsulated within a capsule (e.g., a gelatin or hydroxypropyl methylcellulose capsule).

In some embodiments, provided herein is a method of treating a disease (e.g., hypertension, congestive heart failure, acute myocardial infarction, or diabetic nephropathy) in a subject in need thereof comprising administering an ingestible event marker composition to the subject, wherein the composition comprises:
1) a granule comprising:
about 10.3% w/w lisinopril;
about 15.5% w/w dicalcium phosphate dihydrate;
about 58.6% w/w mannitol (e.g., 180 µm);
about 15.5% w/w pregelatinized starch; and
about 0.15% w/w iron oxide yellow;
2) an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
3) about 0.5% w/w magnesium stearate; and
4) about 5% w/w pregelatinized starch; and
wherein the integrated circuit, wafer and skirt film are coated with a hydroxypropyl cellulose coating, and the granule, identifier magnesium stearate, and pregelatinized starch are encapsulated within a capsule (e.g., a gelatin or hydroxypropyl methylcellulose capsule).

In some embodiments, provided herein is a method of treating a disease (e.g., hypertension, congestive heart failure, acute myocardial infarction, or diabetic nephropathy) in a subject in need thereof comprising administering an ingestible event marker composition to the subject, wherein the composition comprises:
1) a granule comprising:
about 11.2% w/w lisinopril;
about 16.9% w/w dicalcium phosphate dihydrate;
about 60.5% w/w mannitol (e.g., 180 µm);
about 11.2% w/w pregelatinized starch; and
about 0.15% w/w iron oxide yellow; and
2) an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
3) about 0.5% w/w magnesium stearate; and
4) about 5 to about 10% w/w pregelatinized starch; and
wherein the integrated circuit, wafer and skirt film are coated with a hydroxypropyl cellulose coating, and the granule, identifier, magnesium stearate, and pregelatinized starch are encapsulated within a capsule (e.g., a gelatin or hydroxypropyl methylcellulose capsule).

In some embodiments, provided herein is a method of treating a disease (e.g., hypertension, congestive heart failure, acute myocardial infarction, or diabetic nephropathy) in a subject in need thereof comprising administering an ingestible event marker composition to the subject, wherein the composition comprises:
1) a granule comprising:
about 11.2% w/w lisinopril;
about 16.9% w/w dicalcium phosphate dihydrate;
about 60.5% w/w mannitol (e.g., 180 µm);
about 11.2% w/w pregelatinized starch; and
about 0.15% w/w iron oxide yellow; and
2) an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
3) about 0.5% w/w magnesium stearate; and
4) about 5% w/w pregelatinized starch; and
wherein the integrated circuit, wafer and skirt film are coated with a hydroxypropyl cellulose coating, and the granule, identifier, magnesium stearate, and pregelatinized starch are encapsulated within a capsule (e.g., a gelatin or hydroxypropyl methylcellulose capsule).

In some embodiments, provided herein is a method of treating a disease (e.g., hypertension, congestive heart failure, acute myocardial infarction, or diabetic nephropathy) in a subject in need thereof comprising administering an ingestible event marker composition to the subject, wherein the composition comprises:
about 7.3% w/w lisinopril;
about 30.0% w/w dicalcium phosphate dihydrate;
about 24.6% w/w mannitol (e.g., 50 µm);
about 20.0% w/w pregelatinized starch;
about 15.0% w/w microcrystalline cellulose;
about 2.0% w/w croscarmellose sodium;
about 0.15% w/w yellow iron oxide;
about 1.0% w/w magnesium stearate; and
an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
wherein the integrated circuit, wafer and skirt film are coated with a hydroxypropyl cellulose coating.

In some embodiments, provided herein is a method of treating a disease (e.g., hypertension, congestive heart failure, acute myocardial infarction, or diabetic nephropathy) in a subject in need thereof comprising administering an ingestible event marker composition to the subject, wherein the composition comprises:
about 7.3% w/w lisinopril;
about 15.0% w/w dicalcium phosphate dihydrate;
about 24.6% w/w mannitol (e.g., 50 µm);
about 20.0% w/w pregelatinized starch;
about 30.0% w/w microcrystalline cellulose;

about 2.0% w/w croscarmellose sodium;
about 0.15% w/w yellow iron oxide;
about 1.0% w/w magnesium stearate; and
an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
wherein the integrated circuit, wafer and skirt film are coated with a hydroxypropyl cellulose coating.

In some embodiments, provided herein is a method of treating a disease (e.g., hypertension, congestive heart failure, acute myocardial infarction, or diabetic nephropathy) in a subject in need thereof comprising administering an ingestible event marker composition to the subject, wherein the composition comprises:
about 7.3% w/w lisinopril;
about 30.0% w/w dicalcium phosphate dihydrate;
about 24.6% w/w mannitol (e.g., 50 µm);
about 20.0% w/w pregelatinized starch;
about 15.0% w/w microcrystalline cellulose;
about 2.0% w/w croscarmellose sodium;
about 0.15% w/w yellow iron oxide;
about 1.0% w/w magnesium stearate; and
an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
wherein
the integrated circuit, wafer and skirt film are coated with a hydroxypropyl cellulose coating,
the lisinopril, dicalcium phosphate dihydrate, mannitol (e.g., 50 µm), pregelatinized starch, microcrystalline cellulose, croscarmellose sodium, yellow iron oxide, and identifier are compressed to form an inner compressed tablet, and
the magnesium stearate is compressed as an outer compressed shell encapsulating the inner compressed tablet.

In some embodiments, provided herein is a method of treating a disease (e.g., hypertension, congestive heart failure, acute myocardial infarction, or diabetic nephropathy) in a subject in need thereof comprising administering an ingestible event marker composition to the subject, wherein the composition comprises:
about 7.3% w/w lisinopril;
about 15.0% w/w dicalcium phosphate dihydrate;
about 24.6% w/w mannitol (e.g., 50 µm);
about 20.0% w/w pregelatinized starch;
about 30.0% w/w microcrystalline cellulose;
about 2.0% w/w croscarmellose sodium;
about 0.15% w/w yellow iron oxide;
about 1.0% w/w magnesium stearate; and
an identifier comprising:
a) an integrated circuit comprising silicon, aluminum, silicon dioxide, and silicon nitride;
b) a wafer comprising titanium, titanium-tungsten, gold, magnesium, copper (I) chloride, and hydroxypropyl cellulose; and
c) a skirt film comprising ethyl cellulose, hydroxypropyl cellulose, and triethyl citrate;
wherein
the integrated circuit, wafer and skirt film are coated with a hydroxypropyl cellulose coating,
the lisinopril, dicalcium phosphate dihydrate, mannitol (e.g., 50 µm), pregelatinized starch, microcrystalline cellulose, croscarmellose sodium, yellow iron oxide, and identifier are compressed to form an inner compressed tablet, and
the magnesium stearate is compressed as an outer compressed shell encapsulating the inner compressed tablet.

The term "treating" as used herein includes the diagnosis, mitigation, or prevention of progression of a condition or a disease in a subject (e.g., in man or other animals).

EXAMPLES

Example 1 Manufacturing of Power Source and IEM

According to one aspect of the present disclosure, a partial power source may be manufactured as described in detail herein.

A semiconductor substrate may be provided as a chassis which components of the IEM are attached to, deposited upon, and/or secured to. The substrate may be made of silicon. The cathode material may be physically associated with the substrate (e.g., on one side). The cathode material may be chemically deposited on, evaporated onto, secured to, or built-up on the substrate all of which may be referred to herein as "deposit" with respect to the substrate. The cathode material may be deposited on one side of the substrate. The cathode material may be deposited by physical vapor deposition, electrodeposition, or plasma deposition, among other protocols. The cathode material may be from about 0.05 to about 500 µm thick, such as from about 5 to about 100 µm thick. The shape may be controlled by shadow mask deposition, or photolithography and etching. Additionally, there may be more than one electrically unique region on the substrate where the cathode material may be deposited, as desired.

At a different side, which may be the opposite side to the side where the cathode material is deposited, the anode material may be deposited. The different side selected may be the side next to the side selected for the cathode material. The scope of the present disclosure is not limited by the side selected, and the term "different side" can mean any of the multiple sides that are different from the first selected side. Furthermore, the shape of the deposited material(s) may be any geometrically suitable shape. The materials are selected such that they may produce a voltage potential difference when the power source is in contact with conducting liquid, such as body fluids. As indicated above with respect to the cathode material, the anode material may be chemically deposited on, evaporated onto, secured to, or built-up on the substrate. Also, an adhesion layer may be necessary to help the anode material (as well as the cathode material when needed) to adhere to the substrate to provide better electrode contact between the substrate and the electrode material. Typical adhesion layers for the anode material may be Au, Ti, TiW, or similar material. The adhesive layer may have a thickness from 50 Å to 100 Å and up to 1 µm (e.g., about 50 Å to about 1 µm, about 100 Å to about 1 µm, or about 50 Å to about 100 Å). The anode material and the adhesion layer may be deposited by physical vapor deposition, electrodeposition or plasma deposition. The anode material may be from about 0.05 to about 500 µm thick, such as from about 5 to about 100 µm thick. However, the scope of the present disclosure is not limited by the thickness of any of the materials nor by the type of process used to deposit or secure the materials to the substrate.

According to the disclosure set forth, when used with ingestible lisinopril IEM tablets manufactured as described below, the electrode materials are magnesium metal and copper chloride (e.g., copper (I) chloride, CuCl, or cuprous chloride). That is, the anode comprises magnesium metal, and the cathode comprises copper chloride.

In some embodiments, the power source in each lisinopril IEM tablet, manufactured as described below, may include about 0.9 mg of Si, 0.2 mg of Cu, and 0.01 mg of Mg. There is a thick (about 4-8 um, e.g. about 6 µm) layer of gold under the CuCl to increase the surface roughness. The amounts of the materials may be sufficient for generating enough power for the IEM to have a communication time of at least or about 1 minute, e.g., about at least or about 2 minutes, e.g., at least or about 3 minutes, e.g., at least or about 4 minutes, e.g., at least or about 5 minutes, e.g., at least or about 6 minutes, e.g., at least or about 7 minutes, e.g., at least or about 8 minutes, e.g., at least or about 9 minutes, e.g., at least or about 10 minutes, e.g., at least or about 15 minutes, e.g., at least or about 20 minutes, or a range bounded by any of these values. A target communication time may be about 1.5 hours. The power source in each lisinopril IEM tablet may include at least 0.09 mg of Si, 0.02 mg of Cu, and 0.001 mg of Mg. The greater surface areas the electrodes may have, the more power and the stronger signals the IEM may generate, and at the same time, the more materials the power source may have. However, the quantities of the materials used may have to meet the requirements set forth by FDA with respect to the specific elements. Therefore, for example, the maximum amounts of Si, Cu, and Mg, respectively, in each tablet may not exceed the maximum amounts of Si, Cu, and Mg, respectively, as set forth by FDA.

In certain aspects, these two electrode materials may be shielded from the surrounding environment by an additional layer of material. Accordingly, when the shield is dissolved and the two dissimilar materials (magnesium metal and copper chloride) are exposed to the target site, a voltage potential is generated.

Other components of the IEM may be provided as described above.

In some embodiments, the IEM comprises an integrated circuit, a wafer, a skirt, and a coating. In some embodiments, the integrated circuit comprises silicon (Si), aluminum (Al), silicon nitride ($Si_3N_4$), and silicon dioxide ($SiO_2$). In some embodiments, the Al, $Si_3N_4$, and $SiO_2$ exist in multiple thin layers on the surface of a die body (e.g., silicon) to form the electrical interconnects of the integrated circuit. In some embodiments, the integrated circuit further comprises at least one dopant. In some embodiments, the dopant is boron (B). In some embodiments, the IEM comprises the components described in Table 1.

TABLE 1

Exemplary IEM (Ingestible Event Marker) Identifier Composition.

| Source | Component | Density (g/cc) | Area (mm^2) | Thickness (mm) | Fraction (%) | Volume (cc) | Component Mass (g) |
|---|---|---|---|---|---|---|---|
| Integrated circuit | silicon | 2.33 | 1.06 | 0.3 | 96.60% | 3.18E−04 | 7.42E−04 |
| | aluminum | 2.7 | 1.06 | 0.0011 | 0.40% | 1.20E−06 | 3.10E−06 |
| | silicon dioxide | 2.2 | 1.06 | 0.0083 | 2.50% | 8.80E−06 | 1.94E−05 |
| | silicon nitride | 3.1 | 1.06 | 0.00102 | 0.40% | 1.10E−06 | 3.40E−06 |
| | integrated circuit total mass | | | | 19.50% | | 7.68E−04 |
| Wafer | titanium | 4.54 | 1.06 | 0.0002 | 0.80% | 2.12E−07 | 9.63E−07 |
| | titanium-tungsten | 14.44 | 0.81 | 0.00032 | 2.40% | 2.05E−07 | 3.00E−06 |
| | gold | 19.32 | 0.81 | 0.006 | 60.20% | 3.80E−06 | 7.42E−05 |
| | magnesium | 1.74 | 1.06 | 0.008 | 12.00% | 8.50E−06 | 1.48E−05 |
| | copper (I) chloride | 4.14 | 0.74 | 0.0076 | 18.90% | 5.60E−06 | 2.33E−05 |
| | hydroxypropyl cellulose solvent-ethanol (no trace detectable) | 1.1 | 1.06 | 0.006 | 5.70% | 6.40E−06 | 7.00E−06 |
| | wafer total mass | | | | 3.10% | | 1.23E−04 |
| Skirt film | ethyl cellulose | 1.1 | 8.62 | 0.3 | 49.60% | 1.30E−03 | 1.40E−03 |
| | hydroxypropyl cellulose | 1.1 | 8.62 | 0.3 | 30.20% | 7.76E−04 | 8.53E−04 |
| | triethyl citrate solvent-none (extruded) | 1.1 | 8.62 | 0.3 | 20.20% | 5.17E−04 | 5.69E−04 |
| | skirt film total mass | | | | 71.50% | | 2.82E−03 |
| IEM identifier-level coating | hydroxypropyl cellulose solvent-ethanol (no trace detectable) | 1.1 | 7.07 | 0.03 | 100.00% | 2.12E−04 | 2.33E−04 |
| | IEM identifier-level coating total mass | | | | 5.90% | | 2.33E−04 |
| Total IEM identifier mass | | | | | 100.00% | | 3.95E−03 |

Example 2 Manufacturing of Lisinopril IEM Tablets

According to one aspect of the present disclosure, lisinopril IEM tablets may be manufactured using the IEM manufactured in Example 1 and using the processes described in U.S. Pat. No. 8,784,308. An illustration process is described below.

In some embodiments, the lisinopril IEM tablets comprise lisinopril and the components described in Table 1.

Figure 5:
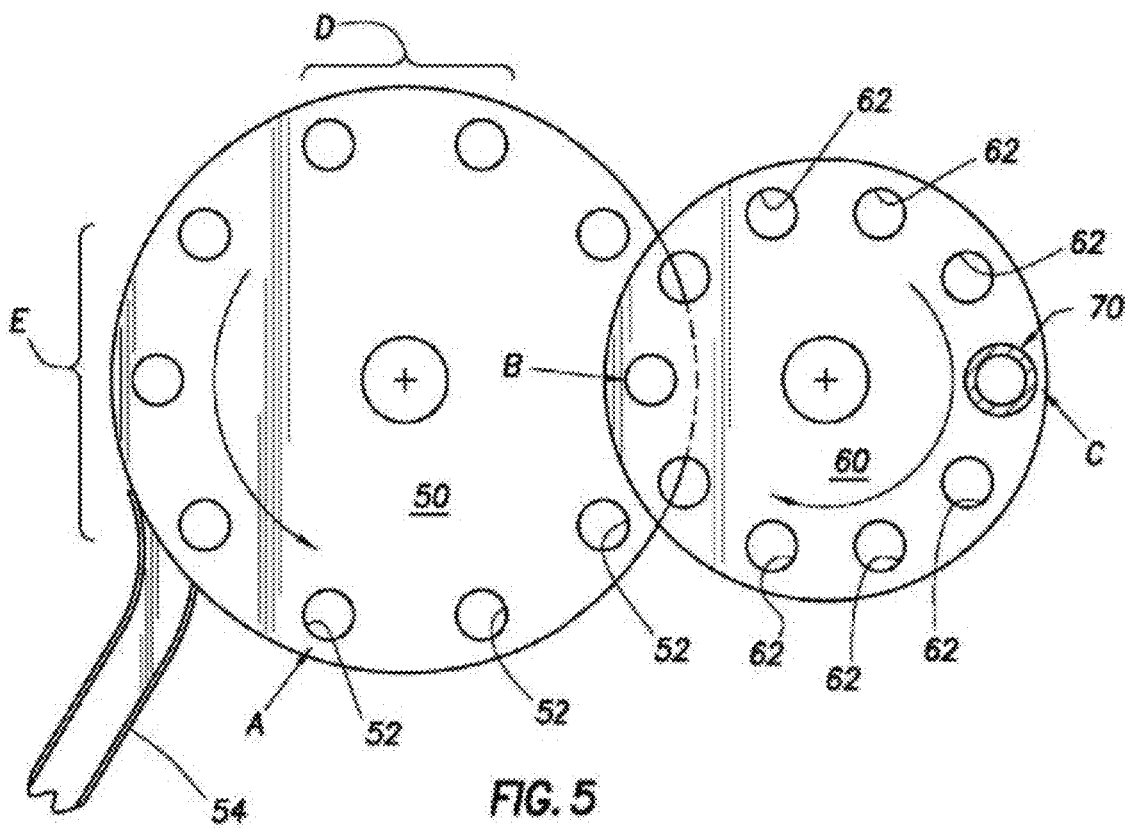
FIG. 5 is an assembling apparatus for assembling a signal generation element on a tablet, according to one aspect of the present disclosure.
Figure 6:
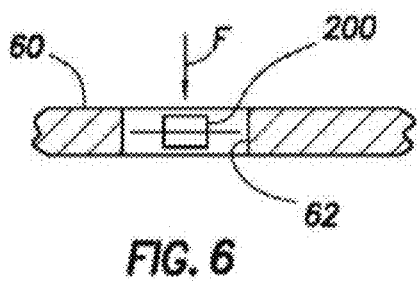
FIG. 6 is a close-up view of a portion of a portion of the apparatus of FIG. 5 with specific indication of the direction of force applied, according to one aspect of the present disclosure.
Figure 7:
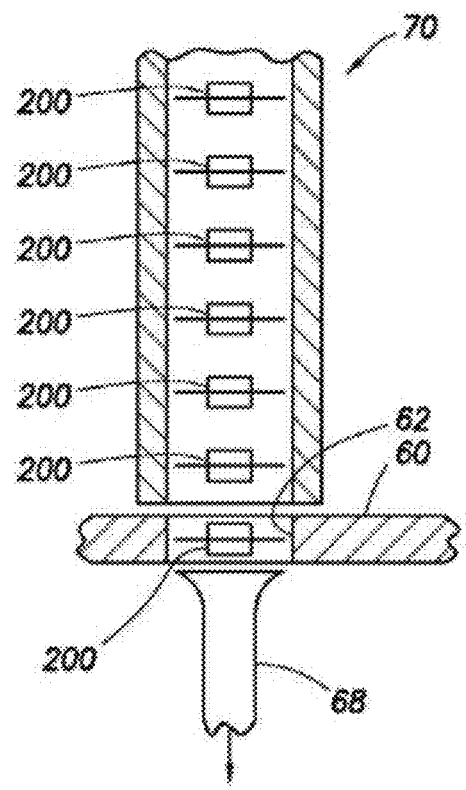
FIG. 7 is a close-up view of a portion of a feeder assembly of the apparatus of FIG. 5, according to one aspect of the present disclosure.

As in FIGS. 5-7, a tablet press 50 is shown. The press 50 may rotate in a counter-clockwise direction as shown. The press 50 may include die cavity or punch cavity 52 and an ejection tray 54. Starting at position A, as shown, the pharmaceutical product, lisinopril, may be deposited in the cavity 52. The press 50 may rotate to position B, which may be positioned below a transfer wheel 60. The wheel 60 may include several openings 62. As the wheel 60 passes position C, each opening 62 may pass under a feeder 70, as shown in FIG. 7.

The feeder 70 may contain marker devices 200. The device 200 may be an IEM that is activated upon contact with a conducting fluid, manufactured as described above in Example 1. The scope of the present disclosure is not limited by the environment or type of the conducting fluid. Once ingested, the device 200 may come into contact with a conducting fluid, such as stomach fluids, and the device 200 may be activated. Referring to the instance where the device 200 is used with the product that is ingested by the living organism, when the product that includes the device 200 is taken or ingested, the device 200 may come into contact with the conducting liquid of the body, a voltage potential may be created, and the device 200 may be activated. A portion of the power source may be provided by the device 200, such as the electrode materials as described above, while another portion of the power source may be provided by the conducting fluid.

Referring again to FIGS. 5 and 6, each time an opening 62 passes under the feeder 70, one of the devices 200 may be dropped into the opening 62 directly under the feeder 70. As shown in FIG. 6, a force "F" is shown to assist the movement of the device 200 from the feeder 70 into the opening 62. The force may be provided by the use of a vacuum through a suction tube 68. In accordance with other aspects of the present disclosure, the force may be provided by a spring, an air burst, or an ejection pin in addition to gravity. The wheel 60 may rotate to position B. At position B, the device 200 located in the opening 62 may be dropped into the cavity 52 of the press 50. The press 50 may rotate to the position D where additional pharmaceutical product may be deposited into the cavity 52 on top of the device 200. The press 50 may continue to move in the counter-clockwise direction and at position E, the content of the cavity 52 may be pressed under high pressure to form a tablet with the device 200 inside. The completed tablet may be ejected and moved to a collection point through the ejection tray 54 for further processing, such as coating layers as needed.

Referring now to FIG. 8, a feeder assembly 72 is shown as alternative embodiment and in accordance with another aspect of the present disclosure. The feeder assembly 72 can be used in place of the feeder 70 of the FIG. 5. The feeder assembly 72 may include a plurality of supporting fingers 74 that hold each device 200 in position. The fingers 74 may be connected to a belt 76. The fingers 74 may lower the device 200 toward the wheel 60 of FIG. 5. When the fingers 74 may reach the lower portion near the wheel 60, the fingers 74 may move apart and drop the device 200 into the opening 62 of the wheel 60.

Referring now to FIG. 9A and FIG. 9B, in accordance with another aspect of the present disclosure, the feeder assembly 72 may include an ejector 73 with a spring 75. As the opening 62 moves under the feeder assembly 72, the ejector 73 may push the device 200 into the opening 62 of the wheel 60.

Example 3 Impact of Core and Mantle on Mechanical Properties and Appearance

This experiment examines the effect of various parameters on the performance of the core, appearance of the core, in particular the formation of stress fractures, and sensor (e.g., identifier) performance of the digimed tablet. Various combinations of mannitol:dicalcium phosphate:magnesium stearate (88:10:2), lactose monohydrate:magnesium stearate (98:2), microcrystalline cellulose (avicel PH102 or PH112), and magnesium stearate were compressed into tablets (5.2 mm diameter and 2.0 mm thick, or 6.5 mm diameter and 2.0 mm thick; shallow-concave tablets) comprising a sensor. The tablets were either a core, or a core with an outer coating. The properties of the tablets were assessed immediately (T zero), 24 hours, 72 hours, 7 days, 15 days, and 30 days post-compression while being stored at 25° C./60% RH and 40° C./75% RH open stress conditions (e.g., an open container).

The following attributes of the tablets were assessed: appearance, weight, thickness, diameter, tensile strength, and moisture. The core that showed the least issues with regard to appearance when studied under 25° C./60% RH and 40° C./75% RH for up to 14 days was a lactose based core. When lactose was combined with either a plastic (Avicel) or another brittle mantle (lactose or Mannitol/DCP), no cracking was observed.

The mannitol/DCP cores showed no cracking at 25° C./60% RH but cracking at 40° C./75% RH when combined with lactose or Avicel mantle. A mannitol/DCP mantle combined with a mannitol/DCP core had a low incidence of cracking in both conditions.

An Avicel core combined with a lactose mantle gave rise to significant cracking in both 25° C./60% RH and 40° C./75% RH. An avicel core combined with mannitol/DCP had a mixed result in that the smaller core 5220 saw significant cracking in both conditions whereas the 6520 size core showed no cracking at either condition. An avicel core and avicel mantle showed no cracking under 25° C./60% RH but some degree of cracking at 40° C./75% RH.

Tablets were placed in a sensor activation media and sensor performance was assessed. The results showed that mannitol:dicalcium phosphate:magnesium stearate cores and lactose:magnesium stearate cores do not pass sensor performance criteria (long activation time [mannitol only] and low peak mean amplitude).

Example 4 Influence of Disintegrant on Sensor Performance in Various Core Formulations This experiment examines the effect of different types of disintegrant and their concentration within the core formulation on sensor performance. Various excipient filler combinations were combined with different disintegrants. The superdisintegarnts; croscarmellose sodium, sodium starch glycolate and crospovidone were individually combined at the 2% concentration level with the following core blend formulations; mannitol:dicalcium phosphate anhydrous:magnesium stearate (86.5:10:1.5), microcrystalline cellulose:magnesium stearate (97.0:1.0), lactose monohydrate:magnesium stearate (96.5:1.5). Pregelatinized starch at the 10% level was evaluated with the following core formulations; mannitol:dicalcium phosphate anhydrous:magnesium stearate (79.75:10:0.25), microcrystalline cellulose:magnesium stearate (89.75:0.25), lactose monohydrate:magnesium stearate (89.75:0.25). Microcrystalline cellulose at the 15% level was investigated with the following core formulations; mannitol:dicalcium phosphate anhydrous:magnesium stearate (73.5:10:1.5), lactose monohydrate:magnesium stearate (83.5:1.5). The tablets were all compressed using round, 5.2 mm diameter shallow concave tooling to a mean thickness of 2 mm.

The tablets were all assessed for sensor performance by placing them in sensor media. The results showed that the mannitol:dicalcium phosphate anhydrous disintegrant combinations and the microcrystalline cellulose disintegrant combinations studied all pass the sensor performance criteria at the disintegrant concentrations used. The lactose disintegrant combinations did pass the sensor performance criteria however this was associated with a high degree of variability and prolonged activation times.

Example 5 Disintegrant Level Optimization in Various Core Formulations

This experiment examines the effect of type and amount of disintegrant included in lactose-based formulations; lactose monohydrate:croscarmellose sodium:magnesium stearate (94.5:4.0;1.5), lactose monohydrate:sodium starch glycolate:magnesium stearate (90.5:8.0;1.5), lactose monohydrate:crospovidone:magnesium stearate (93.5:5.0;1.5), lactose monohydrate:pregelatinized starch:magnesium stearate (79.5:20.0;0.5). The tablets were all assessed for sensor performance by placing them in sensor media. The increase in the amount of disintegrant improved the sensor performance attributes of peak mean amplitude, counts and time to activation, whilst also reducing the overall variability seen with the lactose monohydrate based cores.

Example 6 Die Fall Out (DFO) Propensity of Optimized Core Formulations

This experiment examines the sensor performance and the propensity for Die Fall Out (DFO) of optimized cores within a slowly dissolving (e.g. metformin) mantle. The following cores were compressed using round, 5.2 mm diameter shallow concave tooling; mannitol:dicalcium phosphate anhydrous:croscarmellose sodium:magnesium stearate (86.5:10:2.0:1.5), mannitol:dicalcium phosphate anhydrous:sodium starch glycolate:magnesium stearate (86.5:10:2.0:1.5), mannitol:dicalcium phosphate:starch 1500:magnesium stearate (79.75:10:10:0.25), mannitol:dicalcium phosphate anhydrous:microcrystalline cellulose:magnesium stearate (73.5:10:15:1.5), microcrystalline cellulose (PH102):croscarmellose sodium:magnesium stearate (97.0:2.0:1.5), microcrystalline cellulose (PH102):sodium starch glycolate:magnesium stearate (97.0:2.0:1.5), microcrystalline cellulose (PH102):starch 1500:magnesium stearate (89.75:10:0.25), lactose monohydrate:croscarmellose sodium:magnesium stearate (94.5:4.0;1.5), lactose monohydrate:sodium starch glycolate:magnesium stearate (90.5:8.0;1.5), lactose monohydrate:starch 1500:magnesium stearate (79.75:20.0;0.25). The cores were then compressed inside the metformin mantle using round 10.0 mm diameter tooling. The tablets were all assessed for sensor performance by placing them in sensor media. All cores showed zero DFO except for the microcrystalline cellulose:croscarmellose sodium:magnesium stearate core which showed 4%.

Example 7 Impact of Core Shape on Die Fall Out (DFO)

This experiment investigated whether the shape of the tablet could affect the propensity for DFO observed with different core formulations. The following cores were compressed into flat faced and shallow concave shapes using round 5.2 mm diameter shallow concave and round 5.2 mm diameter flat beveled edge tooling. Microcrystalline cellulose:croscarmellose sodium:magnesium stearate (97:2:1), lactose monohydrate:croscarmellose sodium:magnesium stearate (94.5:4:1.5), mannitol:dicalcium phosphate anhydrous:croscarmellose sodium:magnesium stearate (86.5:10:2:1.5). The cores were then compressed inside a metformin mantle using round 10.0 mm diameter tooling. The resultant tablets were all assessed for sensor performance, in particular DFO by placing them in sensor media. The lactose and mannitol:dicalcium phosphate anhydrous based cores showed no DFO in combination with the croscarmellose sodium disintegrant for either tablet shape; flat faced beveled edge and shallow concave. The combination of microcrystalline cellulose and croscarmellose sodium showed DFO for both tooling shapes with the FFBE shape having a higher incidence of 22% compared to 7% for the shallow concave. The following cores were compressed using 5.2 mm flat faced beveled edge tooling and then compressed inside a metformin mantle using round 10.0 mm diameter tooling before being assessed for sensor performance, in particular DFO by placing them in sensor media. Microcrystalline cellulose:sodium starch glycolate:magnesium stearate (97:2:1), Microcrystalline cellulose:starch 1500:magnesium stearate (89.75:10:0.25), lactose monohydrate:sodium starch glycolate:magnesium stearate (90.5:8:1.5), lactose monohydrate:starch 1500:magnesium stearate (79.75:20:0.25), mannitol:dicalcium phosphate anhydrous:sodium starch glycolate:magnesium stearate (86.5:10:2:1.5), mannitol:dicalcium phosphate anhydrous:starch 1500:magnesium stearate (79.75:10:0.25), mannitol:dicalcium phosphate anhydrous:microcrystalline cellulose:magnesium stearate (73.5:10:15:1.5). None of the cores tested showed DFO.

Example 8 Impact of Compaction Pressure on Tensile Strength, Solid Fraction, and Sensor Performance of Core Formulations Core tablet formulations were compressed over a range of compaction pressures in order to assess the impact on sensor performance. Mannitol:dicalcium phosphate anhydrous:microcrystalline cellulose:magnesium stearate (73.5:10:15:1.5), lactose monohydrate:croscarmellose sodium:magnesium stearate (94.5:4:1.5) and microcrystalline cellulose:croscarmellose sodium:magnesium stearate (97:2:1) were all compressed using round 5.2 mm diameter flat faced beveled edge tooling. The sensor performance of the cores was assessed by placing them in sensor media. The results showed that as the compaction pressure increased the time to activation increased with the most significant increases seen with the lactose based core. The other sensor attributes peak mean amplitude and counts passed performance criteria at all compaction pressures.

Mannitol:dicalcium phosphate anhydrous:microcrystalline cellulose:magnesium stearate (73.5:10:15:1.5), compressed using a compaction pressure of 209 N/mm², lactose monohydrate:croscarmellose sodium:magnesium stearate (94.5:4:1.5) compressed using a compaction pressure of 209 N/mm² and microcrystalline cellulose:croscarmellose sodium:magnesium stearate (97:2:1) compressed using a compaction pressure of 168 N/mm² were compressed inside two different lisinopril mantles (A5 and B5 as per Table 3).

The resultant lisinopril SP tablets for both the lisinopril A5 and B5 formulations were assessed for appearance, sensor performance and dissolution. No major cracks were observed for either formulation as a result of storage in an open container in 25° C./60% RH for up to 7 days. The dissolution in 900 mL of 0.1N HCl (50 rpm, paddle method) showed that the B series lisinopril SP tablet released the drug much faster than the A series and so more closely matched the Reference Product. The sensor performance was assessed in sensor media and showed that the for the A and B Lisinopril products no DFO was observed with any of the cores investigated. Lisinopril SP tablet made with the B series had much better sensor performance attributes in terms of activation time, peak mean amplitude and counts than the A series.

Example 9 Impact of Optimized Core Formulations on Tensile Strength, Friability, Sensor Performance, and Die Fall Out (DFO)

This experiment investigated alternate core formulations which were optimized for compaction properties. The effect of lubrication time on the tensile strength, friability and sensor performance (peak mean amplitude and counts) was assessed. Table 2 below shows the core formulations studied.

tivity to lubrication time in that the tensile strength of the resultant tablets after prolonged mixing showed a decrease. Core 9 however although similar to core 3, appeared to overcome the tensile strength lubricant sensitivity issue by the addition of silicon dioxide to the formulation.

Core 8 showed inferior sensor performance compared to the other cores tested.

The tensile strength of cores 4 and 5 was not sensitive to the extended lubrication times and both showed good sensor performance in sensor media.

The tensile strength of core 6 showed some sensitivity to lubrication time in that the prolonged mixing time had a negative effect, two revised formulations were therefore evaluated. One had the addition of 1.5% silicon dioxide and the other saw the removal of the microcrystalline cellulose component to give the following formulations; lactose monohydrate:microcrystalline cellulose:silicon dioxide:croscarmellose sodium:magnesium stearate (64:30:1.5:4:0.5) and lactose monohydrate:croscarmellose sodium:magnesium stearate (95.5:4:0.5). Cores were compressed using round 5.2 mm diameter flat faced beveled edge tooling. Both formulations no longer demonstrated sensitivity to lubrication time in terms of a negative effect on tensile strength.

Core 5 (mannitol:dicalcium phosphate anhydrous:croscarmellose sodium:magnesium stearate (67.5:30:2:0.5)), two lactose based cores, lactose monohydrate:microcrystalline cellulose:silicon dioxide:croscarmellose sodium:magnesium stearate (64:30:1.5:4:0.5) and lactose monohydrate:croscarmellose sodium:magnesium stearate (95.5:4:0.5) and core 9 (microcrystalline cellulose:mannitol:silicon dioxide:croscarmellose sodium:magnesium stearate (66:30:1.5:2:0.5) were all compressed using round 5.2 mm diameter flat faced beveled edge tooling and then compressed inside the metformin mantle using round 10.0 mm diameter tooling to assess the propensity for DFO in sensor media. Both core 5 and the lactose monohydrate:microcrystalline cellulose:sili-

TABLE 2

| Cores | Primary Filler (% w/w) | Secondary Filler (% w/w) | Tertiary Filler (% w/w) | Disintegrant (% w/w) | Lubricant (% w/w) |
|---|---|---|---|---|---|
| Core #1 | 89.5% microcrystalline cellulose | 10% Dibasic calcium phosphate anhydrous | None | None | 0.5% Magnesium stearate |
| Core #2 | 87.5% microcrystalline cellulose | 10% Dibasic calcium phosphate anhydrous | None | 2% Sodium Starch Glycolate | |
| Core #3 | 67.5% microcrystalline cellulose | 30% Mannitol | None | 2% Croscarmellose Sodium | |
| Core #4 | 57.5% Mannitol | 10% Dibasic calcium phosphate anhydrous | 30% microcrystalline cellulose | 2% Croscarmellose Sodium | |
| Core #5 | 67.5% Mannitol | 30% microcrystalline cellulose | None | 2% Croscarmellose Sodium | |
| Core #6 | 65.5% Lactose | 30% microcrystalline cellulose | None | 4% Croscarmellose Sodium | |
| Core #7 (control) | 84% microcrystalline cellulose | 10% Dibasic calcium phosphate anhydrous | 1.5% Silicon Dioxide | 4% Croscarmellose Sodium | |
| Core #8 | 98% microcrystalline cellulose | None | 1.5% Silicon Dioxide | None | |
| Core #9 | 66% microcrystalline cellulose | 30% Mannitol | 1.5% Silicon Dioxide | 2% Croscarmellose Sodium | |

Tablet cores were compressed using round 5.2 mm diameter flat faced beveled edge tooling.

Cores 1, 2 and 3 which have the majority of the formulation based on microcrystalline cellulose all showed sensicon dioxide:croscarmellose sodium:magnesium stearate (64:30:1.5:4:0.5) core showed a low incidence of DFO 8% and 3% respectively. None of the other cores showed any DFO.

Example 10 Exemplary Compositions

Table 3 shows exemplary compositions provided herein and their corresponding physical, mechanical, and electrical characteristics. Each of the formulations of Table 3 includes an IEM identifier. Table 4 shows exemplary compositions provided herein, which may be in SP TAB, IEM TAB, or SP CAP form.

TABLE 3

Exemplary formulations.

| Formulation | Component (% w/w) Dose Form | IEM-identifier Sensor alone | B5 SP TAB | A5 SP TAB | A5 SP TAB |
|---|---|---|---|---|---|
| Intragranular | lisinopril | — | 7.30% | 10.00% | 10.00% |
| | dicalcium phosphate, dihydrate | — | 30.00% | 15.00% | 15.00% |
| | dicalcium phosphate | — | — | — | — |
| | mannitol (50 um) | — | 24.60% | 53.85% | 53.85% |
| | mannitol (180 um) | — | — | — | — |
| | pregelatinized starch | — | 20.00% | 10.00% | 10.00% |
| | microcrystalline cellulose | — | 15.00% | — | — |
| | croscarmellose sodium | — | 2.00% | — | — |
| | yellow iron oxide | — | 0.15% | 0.15% | 0.15% |
| | FD&C yellow #6 | — | — | — | — |
| Extra-granular | pregelatinized starch | — | — | 10.00% | 10.00% |
| | magnesium stearate | — | 1.00% | 1.00% | 1.00% |
| | croscarmellose sodium | — | — | — | — |
| Core Blend | | — | SP1 | Mannitol/ dicalcium phosphate/ microcrystalline cellulose | Lactose/ croscarmellose sodium |
| Bulk density (g/mL) | | NA | 0.68 | 0.66 | 0.66 |
| Tapped density (g/mL) | | NA | 0.85 | 0.75 | 0.75 |
| Appearance - cracks? (sensor pill tablet includes IEM-identifier) | | NA | Yes | Yes | No |
| Appearance - cracks? (IEM-identifier not in tablet) | | NA | none | NA | NA |
| Activation time (s) | | 42 ± 13 | 499 | 745 ± 107 | 944 ± 144 |
| Peak Mean Amplitude | | 189 ± 32 | 123 | 155 ± 49 | 149 ± 50 |
| Signal counts | | 99 ± 12 | 93 | 164 ± 33 | 127 ± 53 |
| Median Frequency | | 12760 ± 90 | NA | NA | NA |
| Minimum disintegration time (s) | | NA | NA | 492 | 685 |
| Maximum disintegration time (s) | | NA | NA | 587 | 735 |
| Hardness (kP) | | NA | 13.7 | 11.2 | 15.6 |
| Compaction pressure (N/mm^2) | | NA | 122 | 227 | 227 |

TABLE 3-continued

Exemplary formulations.

| | | | | | |
|---|---|---|---|---|---|
| Tensile Strength (N/mm^2) | | NA | 0.49 | 1.42 | 1.92 |
| Friability | | NA | Pass | Pass | Pass |
| Overall Performance | | Acceptable | Mechanical cracking | Long activation | Long activation |
| Formulation | Component (% w/w) | A5 | B5 | B5 | B5 |
| | Dose form | SP TAB | SP TAB | SP TAB | SP TAB |
| Intragranular | lisinopril | 10.00% | 7.30% | 7.30% | 7.30% |
| | dicalcium phosphate, dihydrate | 15.00% | 30.00% | 30.00% | 30.00% |
| | dicalcium phosphate | — | — | — | — |
| | mannitol (50 um) | 53.85% | 24.60% | 24.60% | 24.60% |
| | mannitol (180 um) | — | — | — | — |
| | pregelatinized starch | 10.00% | 20.00% | 20.00% | 20.00% |
| | microcrystaline cellulose | — | 15.00% | 15.00% | 15.00% |
| | croscarmellose sodium | — | 2.00% | 2.00% | 2.00% |
| | yellow iron oxide | 0.15% | 0.15% | 0.15% | 0.15% |
| | FD&C yellow #6 | — | — | — | — |
| Extragranular | pregelatinized starch | 10.00% | — | — | — |
| | magnesium stearate | 1.00% | 1.00% | 1.00% | 1.00% |
| | croscarmellose sodium | — | — | — | — |
| | Polyvinylpyrrolidone | — | — | — | — |
| Core Blend | Main filler | Avicel/ AcDiSol | Mannitol/ DCP/ Avicel | Lactose/ AcDiSol | Avicel/ AcDiSol |
| Bulk density (g/mL) | | 0.66 | 0.68 | 0.68 | 0.68 |
| Tapped density (g/mL) | | 0.75 | 0.74 | 0.74 | 0.74 |
| Appearance - cracks? (sensor pill tablet includes IEM-identifier) | | No | Yes | No | Yes |
| Appearance - cracks? (IEM-identifier not in tablet) | | NA | NA | NA | NA |
| Activation time (s) | | 925 ± 116 | 219 ± 52 | 341 ± 56 | 280 ± 46 |
| Peak Mean Amplitude | | 185 ± 37 | 180 ± 44 | 197 ± 33 | 234 ± 27 |
| Signal counts Median Frequency | | 106 ± 29 | 157 ± 31 | 130 ± 36 | 93 ± 18 |
| Minimum disintegration time (s) | | 638 | 59 | 62 | 63 |
| Maximum disintegration time (s) | | 714 | 90 | 85 | 78 |
| Hardness (kP) | | 10.8 | 13.2 | 10.4 | 9.7 |
| Compaction pressure (N/mm^2) | | 227 | NA | NA | NA |
| Tensile Strength (N/mm^2) | | 1.32 | NA | NA | NA |
| Friability | | Pass | Pass | Pass | Pass |
| Overall Performance | | Long activation | Minor cracking | Acceptable | Minor cracking |

TABLE 3-continued

Exemplary formulations.

| Formulation | Component (% w/w) | A4 | A4 + AcDiSol | A4 + Starch | A5 + Starch |
|---|---|---|---|---|---|
| | Dose form | IEM TAB | IEM TAB | IEM TAB | IEM TAB |
| Intragranular | lisinopril | 10.21% | 9.69% | 9.18% | 10.00% |
| | dicalcium phosphate, dihydrate | 15.31% | 14.53% | 13.76% | 15.00% |
| | dicalcium phosphate | — | — | — | — |
| | mannitol (50 um) | — | — | — | — |
| | mannitol (180 um) | 58.02% | 55.09% | 52.16% | 53.85% |
| | pregelatinized starch | 15.31% | 14.53% | 13.76% | 10.00% |
| | microcrystalline cellulose | — | — | — | — |
| | croscarmellose sodium | — | — | — | — |
| | yellow iron oxide | 0.16% | 0.15% | 0.14% | 0.15% |
| | FD&C yellow #6 | — | — | — | — |
| Extragranular | pregelatinized starch | — | — | 10.00% | 10.00% |
| | magnesium stearate | 1.00% | 1.00% | 1.00% | 1.00% |
| | croscarmellose sodium | — | 5.00% | — | — |
| | polyvinylpyrrolidone | — | — | — | — |
| Core Blend | Main filler | not applicable | not applicable | not applicable | not applicable |
| Bulk density (g/mL) | | 0.66 | 0.66 | 0.66 | 0.69 |
| Tapped density (g/mL) | | 0.78 | 0.78 | 0.78 | 0.78 |
| Appearance - cracks? (sensor pill tablet includes IEM-identifier) | | None | None | None | None |
| Appearance - cracks? (IEM-identifier not in tablet) | | NA | NA | NA | NA |
| Activation time (s) | | 1028 | 826 | 879 | 641 |
| Peak Mean Amplitude (uV) | | 183 | 185 | 53 | 205 |
| Signal counts | | NA | 55 | NA | 127 |
| Median Frequency | | 12659 | 12760 | 12427 | 12723 |
| Minimum disintegration time (s) | | NA | NA | 600 | 240 |
| Maximum disintegration time (s) | | NA | NA | 900 | 540 |
| Hardness (kP) | | 11.7 | 10.2 | 8.1 | 4.3 |
| Compaction pressure (N/mm^2) | | 113 | 113 | 113 | 345 |
| Tensile Strength (N/mm^2) | | 1.58 | 1.36 | 1.00 | 1.24 |
| Friability | | NA | NA | Pass | Minor edge |
| Overall Performance | | Long activation | Long activation | Long activation | Borderline mechanical |
| Formulation | Component (% w/w) | A6a | A6b | B5 | B6 |
| | Dose form | IEM TAB | IEM TAB | IEM TAB | IEM TAB |
| Intragranular | lisinopril | 18.18% | 18.18% | 7.27% | 10.00% |
| | dicalcium phosphate, dihydrate | 13.18% | 14.32% | 30.00% | 28.00% |
| | dicalcium phosphate | — | — | — | — |
| | mannitol (50 um) | 47.50% | 51.36% | 24.58% | 22.85% |
| | mannitol (180 um) | — | — | — | — |
| | pregelatinized starch | 10.00% | 5.00% | 20.00% | 20.00% |
| | microcrystalline cellulose | — | — | 15.00% | 16.00% |

TABLE 3-continued

Exemplary formulations.

|  |  |  |  |  |  |
|---|---|---|---|---|---|
|  | croscarmellose sodium | — | — | 2.00% | 2.00% |
|  | yellow iron oxide | 0.14% | 0.14% | 0.15% | 0.15% |
|  | FD&C yellow #6 | — | — | — | — |
| Extragranular | pregelatinized starch | 10.00% | 10.00% | — | — |
|  | magnesium stearate | 1.00% | 1.00% | 1.00% | 1.00% |
|  | croscarmellose sodium | — | — | — | — |
|  | Polyvinylpyrrolidone | — | — | — | — |
| Core Blend | Main filler | not applicable | not applicable | not applicable | not applicable |
| Bulk density (g/mL) |  | 0.67 | 0.63 | 0.68 | 0.65 |
| Tapped density (g/mL) |  | 0.76 | 0.82 | 0.74 | 0.75 |
| Appearance - cracks? (sensor pill tablet includes IEM-identifier) |  | None | None | None | None |
| Appearance - cracks? (IEM-identifier not in tablet) |  | NA | NA | NA | NA |
| Activation time (s) |  | 625 | 572 | 272 | 500 |
| Peak Mean Amplitude |  | 182 | 188 | 213 | 198 |
| Signal counts |  | 129 | 139 | 125 | 116 |
| Median Frequency |  | 12804 | 12826 | 12679 | 12851 |
| Minimum disintegration time (s) |  | 180 | 240 | 60 | 120 |
| Maximum disintegration time (s) |  | 660 | 540 | 240 | 180 |
| Hardness (kP) |  | 9.0 | 8.6 | 9.71 | 11.51 |
| Compaction pressure (N/mm^2) |  | 223 | 223 | 118 | 170 |
| Tensile Strength (N/mm^2) |  | 2.11 | 2.07 | 0.48 | 1.05 |
| Friability |  | Pass | Pass | Pass | Pass |
| Overall Performance |  | Acceptable | Acceptable | Acceptable | Acceptable |

| Formulation | Component (% w/w) | A4a | A4b | A4c | A4d |
|---|---|---|---|---|---|
|  | Dose Form | SP CAP | SP CAP | SP CAP | SP CAP |
| Intragranular | lisinopril | 10.26% | 10.16% | 10.05% | 10.10% |
|  | dicalcium phosphate, dihydrate | 15.38% | 15.23% | 15.07% | 15.15% |
|  | dicalcium phosphate | — | — | — | — |
|  | mannitol (50 um) | — | — | — | — |
|  | mannitol (180 um) | 58.32% | 57.73% | 57.14% | 57.44% |
|  | pregelatinized starch | 15.38% | 15.23% | 15.07% | 15.15% |
|  | microcrystalline cellulose | — | — | — | — |
|  | croscarmellose sodium | — | — | — | — |
|  | yellow iron oxide | 0.15% | 0.15% | 0.15% | 0.15% |
|  | FD&C yellow #6 | — | — | — | — |
| Extragranular | pregelatinized starch | — | — | — | — |
|  | magnesium stearate | 0.50% | 0.50% | 0.50% | 1.00% |
|  | croscarmellose sodium | — | 1.00% | 2.00% | 1.00% |

TABLE 3-continued

Exemplary formulations.

| | | | | |
|---|---|---|---|---|
| Bulk density (g/mL) | NA | NA | NA | NA |
| Tapped density (g/mL) | NA | NA | NA | NA |
| Appearance - cracks? (sensor pill tablet includes IEM-identifier) | not applicable | not applicable | not applicable | not applicable |
| Appearance - cracks? (IEM-identifier not in tablet) | not applicable | not applicable | not applicable | not applicable |
| Activation time (s) | 169 ± 48 | 173 ± 31 | 187 ± 42 | 198 ± 54 |
| Peak Mean Amplitude | 167 ± 27 | 168 ± 25 | 178 ± 27 | 176 ± 31 |
| Signal counts | 78 ± 10 | 80 ± 10 | 78 ± 12 | 77 ± 12 |
| Median Frequency | 12669 ± 78 | 12673 ± 83 | 12692 ± 61 | 12679 ± 69 |
| Minimum disintegration time (s) | 105 | 75 | 97 | 71 |
| Maximum disintegration time (s) | 333 | 263 | 313 | 261 |
| Hardness (kP) | not applicable | not applicable | not applicable | not applicable |
| Compaction pressure (N/mm^2) | not applicable | not applicable | not applicable | not applicable |
| Tensile Strength (N/mm^2) | not applicable | not applicable | not applicable | not applicable |
| Friability | not applicable | not applicable | not applicable | not applicable |
| Overall Performance | Acceptable | Acceptable | Acceptable | Acceptable |

| Formulation | Component (% w/w) Dose form | A4e SP CAP | A4f SP CAP | A5a SP CAP | A5b SP CAP |
|---|---|---|---|---|---|
| Intragranular | lisinopril | 10.00% | 9.74% | 10.62% | 10.06% |
| | dicalcium phosphate, dihydrate | 15.00% | 14.61% | 15.92% | 15.08% |
| | dicalcium phosphate | — | — | — | — |
| | mannitol (50 um) | — | — | — | — |
| | mannitol (180 um) | 56.85% | 55.39% | 57.18% | 54.16% |
| | pregelatinized starch | 15.00% | 14.61% | 10.62% | 10.06% |
| | microcrystalline cellulose | — | — | — | — |
| | croscarmellose sodium | — | — | — | — |
| | yellow iron oxide | 0.15% | 0.14% | 0.14% | 0.13% |
| | FD&C yellow #6 | — | — | — | — |
| Extragranular | pregelatinized starch | | 5.00% | 5.00% | 10.00% |
| | magnesium stearate | 1.00% | 0.50% | 0.50% | 0.50% |
| | croscarmellose sodium | 2.00% | — | — | — |
| Bulk density (g/mL)* | | 0.66 | 0.66 | 0.66 | 0.66 |
| Tapped density (g/mL)* | | 0.79 | 0.79 | 0.75 | 0.75 |

TABLE 3-continued

Exemplary formulations.

| | | | | |
|---|---|---|---|---|
| Appearance - cracks? (sensor pill tablet includes IEM-identifier) | not applicable | not applicable | not applicable | not applicable |
| Appearance - cracks? (IEM-identifier not in tablet) | not applicable | not applicable | not applicable | not applicable |
| Activation time (s) | 193 ± 41 | 156 ± 38 | 168 ± 37 | 209 ± 50 |
| Peak Mean Amplitude | 180 ± 24 | 187 ± 35 | 183 ± 33 | 178 ± 22 |
| Signal counts | 75 ± 10 | 73 ± 10 | 115 ± 14 | 72 ± 23 |
| Median Frequency | 12696 ± 81 | 12672 ± 72 | 12942 ± 82 | 12685 ± 75 |
| Minimum disintegration time (s) | 83 | NA | NA | NA |
| Maximum disintegration time (s) | 363 | NA | NA | NA |
| Hardness (kP) | not applicable | not applicable | not applicable | not applicable |
| Compaction pressure (N/mm^2) | not applicable | not applicable | not applicable | not applicable |
| Tensile Strength (N/mm^2) | not applicable | not applicable | not applicable | not applicable |
| Friability | not applicable | not applicable | not applicable | not applicable |
| Overall Performance | Acceptable | Acceptable | Acceptable | Acceptable |

*Note: densities based on intragranular components only. NA = Not Available.

TABLE 4

Exemplary formulations.

| | B6 (F) | | B6 (P) | | B7 (P) | | A6-a (P) | | A6-b (F) | |
|---|---|---|---|---|---|---|---|---|---|---|
| Formulation Components | Dose (mg) | Total % w/w | Dose (mg) | Total % w/w | Dose (mg) | Total % w/w | Dose (mg) | Total % w/w | Dose (mg) | Total % w/w |
| Lisinopril API | 40 | 7.27 | 40 | 10 | 10 | 5 | 40 | 18.18 | 40 | 18.18 |
| Dicalcium Phosphate | 82.5 | 15 | 112 | 28 | 61 | 30.5 | 29 | 13.18 | 31.5 | 14.32 |
| Mannitol | 135.18 | 24.58 | 91.4 | 22.85 | 50.7 | 25.35 | 104.5 | 47.5 | 113 | 51.36 |
| Pregelatinized Starch | 110 | 20 | 80 | 20 | 40 | 20 | 22 | 10 | 11 | 5 |
| Microcrystalline Cellulose | 165 | 30 | 64 | 16 | 32 | 16 | 0 | 0 | 0 | 0 |
| Croscarmellose Sodium | 11 | 2 | 8 | 2 | 4 | 2 | 0 | 0 | 0 | 0 |
| Iron Oxide | 0.83 | 0.15 | 0.6 | 0.15 | 0.3 | 0.15 | 0.3 | 0.14 | 0.3 | 0.14 |
| FD&C yellow #6 | 0 | 0 | 0 | 0 | 0 | 0 | 0 | 0 | 0 | 0 |
| Pregelatinized Starch (extra-granular) | 0 | 0 | 0 | 0 | 0 | 0 | 22 | 10 | 22 | 10 |
| Magnesium Stearate (extra-granular) | 5.5 | 1 | 4 | 1 | 2 | 1 | 2.2 | 1 | 2.2 | 1 |
| Total (mantle) | 550 | 100 | 400 | 100 | 200 | 100 | 220 | 100 | 220 | 100 |

Example 11 Chemical Stability Analysis

Assay and related substances: samples and standards were prepared in 20:80 v/v methanol:water at a nominal lisinopril concentration of 0.4 mg/mL and a 5 µL aliquot analyzed by high performance liquid chromatography (HPLC) using the following conditions:

Column: HALO C8, 3.0 mm×75 mm, 2.7 µm (Advanced Materials Technology Inc., Wilmington, Del., USA);
Mobile phase: isocratic; 81:19 v/v water:acetonitrile containing 0.1% v/v trifluoroacetic acid;
Mobile phase flow rate: 0.8 mL/min;
Column temperature: 15° C.; and
Detector: ultraviolet detection at 215 nm.

Dissolution: samples were tested using USP II (Paddle) dissolution apparatus using 500 mL of 0.01N hydrochloric acid at 37° C. as dissolution medium and a rotational speed of 75 r.p.m. At each specified time point (5 min, 10 min, 15 min and 30 min), 1.5 mL of sample was filtered and analyzed using the same HPLC conditions as for assay and related substances.

The stability of lisinopril in certain of the compositions provided herein was assessed. The dissolution rate of lisinopril in certain of the compositions provided herein was also assessed. Lisinopril is known to degrade to (2S)-2-[(3S,8aR)-3-(4-aminobutyl)-1,4-dioxo-6,7,8,8a-tetrahydro-3H-pyrrolo[1,2-a]pyrazin-2-yl]-4-phenylbutanoic acid. It has been discovered that the compositions provided herein comprise less than about 0.30% (2S)-2-[(3S,8aR)-3-(4-aminobutyl)-1,4-dioxo-6,7,8,8a-tetrahydro-3H-pyrrolo[1,2-a]pyrazin-2-yl]-4-phenylbutanoic acid (diketopiperazine) (DKP) impurity after at least six months of storage.

Table 5a describes the formulations used in Table 5b and Table 5c, which show percentage of dissolution of certain of the SP TAB lisinopril compositions provided herein at time zero (initial preparation of the composition) and six months after the initial preparation of the compositions. Table 6 (lisinopril) and Table 7 (DKP impurity) show the results of chemical stability analysis of the SP TAB lisinopril compositions of Tables 5b-c at time zero and six months. Although other lisinopril degradation impurities are known, only the DKP impurity was detected.

Table 8a describes the formulations used in Table 8b, which shows percentage of dissolution of certain of the IEM TAB lisinopril compositions provided herein at time zero (initial preparation of the composition) and six months after the initial preparation of the compositions. Table 9 (lisinopril) and Table 10 (diketopiperazine impurity) show the results of chemical stability analysis of the IEM TAB lisinopril compositions of Tables 8b at time zero and six months. Although other lisinopril degradation impurities are known, only the DKP impurity was detected.

TABLE 5a

Formulations of Table 5b and Table 5c.

| Reference | Formulation | SP Core | Strength (mg lisinopril) | Desiccant Mass (g) |
|---|---|---|---|---|
| A6a-9-40-1 | A6a with 10% starch | 9 | 40 | 1 |
| A6a-9-40-3 | | 9 | 40 | 3 |
| A6a-5B-40-1 | | 5B | 40 | 1 |
| A6a-5B-40-3 | | 5B | 40 | 3 |
| B7-5B-10-2 | B7 | 5B | 10 | 2 |
| B7-9-10-2 | | 9 | 10 | 2 |
| B6-5B-40-2 | B6 | 5B | 40 | 2 |
| B6-5B-40-4 | | 5B | 40 | 4 |

TABLE 5b

Dissolution of selected SP TAB formulations.

Mean Result (% dissolved)
(Range shown in brackets)

| Time Point (min) | A6a-9-40-1 Initial | A6a-9-40-1 6 months | A6a-9-40-3 Initial | A6a-9-40-3 6 months | A6a-5B-40-1 Initial | A6a-5B-40-1 6 months | A6a-5B-40-3 Initial | A6a-5B-40-3 6 months |
|---|---|---|---|---|---|---|---|---|
| 5 | 84.6 (73.6-91.2) | 92.4 (84.6-97.2) | 84.6 (73.6-91.2) | 87.8 (60.9-98.5) | 89.8 (81.7-101.0) | 87.3 (82.2-93.3) | 89.8 (81.7-101.0) | 93.4 (86.1-101.4) |
| 10 | 94.4 (91.6-100.0) | 95.9 (93.9-100.5) | 94.4 (91.6-100.0) | 98.4 (94.4-101.0) | 99.5 (96.0-104.5) | 95.4 (90.4-97.8) | 99.5 (96.0-104.5) | 99.1 (93.2-102.4) |
| 15 | 95.9 (92.9-101.7) | 96.7 (94.9-101.3) | 95.9 (92.9-101.7) | 99.1 (95.1-100.8) | 100.9 (98.2-105.3) | 96.8 (92.7-100.6) | 100.9 (98.2-105.3) | 100.2 (95.2-103.3) |
| 30 | 98.4 (96.0-104.4) | 98.3 (95.7-102.5) | 98.4 (96.0-104.4) | 99.8 (96.5-102.4) | 102.4 (98.9-104.9) | 98.1 (95.0-102.7) | 102.4 (98.9-104.9) | 101.7 (97.4-104.3) |

TABLE 5c

Dissolution of selected SP TAB formulations.

Mean Result (% dissolved)
(Range shown in brackets)

| Time Point (min) | B7-5B-10-2 Initial | B7-5B-10-2 6 months | B7-9-10-2 Initial | B7-9-10-2 6 months | B6-5B-40-2 Initial | B6-5B-40-2 6 months | B6-5B-40-4 Initial | B6-5B-40-4 6 months |
|---|---|---|---|---|---|---|---|---|
| 5 | 89.9 (84.0-95.1) | 87.1 (77.1-96.5) | 88.4 (74.3-100.0) | 91.7 (79.3-99.8) | 82.4 (68.8-92.1) | 89.4 (84.0-95.8) | 82.4 (68.8-92.1) | 95.6 (93.9-98.7) |

TABLE 5c-continued

Dissolution of selected SP TAB formulations.

Mean Result (% dissolved)
(Range shown in brackets)

| Time Point (min) | B7-5B-10-2 Initial | B7-5B-10-2 6 months | B7-9-10-2 Initial | B7-9-10-2 6 months | B6-5B-40-2 Initial | B6-5B-40-2 6 months | B6-5B-40-4 Initial | B6-5B-40-4 6 months |
|---|---|---|---|---|---|---|---|---|
| 10 | 92.5 (88.5-96.9) | 91.3 (84.7-98.9) | 93.9 (85.9-101.0) | 97.1 (93.7-101.8) | 92.6 (88.4-100.3) | 91.2 (87.9-96.5) | 92.6 (88.4-100.3) | 98.1 (96.2-101.4) |
| 15 | 93.5 (90.0-98.0) | 93.1 (87.5-99.6) | 94.6 (88.6-101.2) | 98.6 (96.0-102.6) | 92.9 (89.4-100.7) | 93.9 (90.1-98.1) | 93.9 (89.4-100.7) | 98.9 (97.0-102.3) |
| 30 | 96.1 (93.7-100.4) | 97.4 (93.4-101.1) | 96.3 (92.4-101.8) | 100.7 (99.3-103.8) | 95.4 (91.5-101.6) | 95.4 (92.6-99.7) | 95.4 (91.5-101.6) | 100.2 (97.9-103.4) |

TABLE 6

Lisinopril assay.

| Sample | Time Point | Mean Result (% label claim) (Replicate results shown in brackets) |
|---|---|---|
| A6a-9-40-1 | Initial | 98.9 (99.6, 98.2) |
| | 6 months | 96.2 (97.6, 94.8) |
| A6a-9-40-3 | Initial | 98.9 (99.6, 98.2) |
| | 6 months | 98.8 (96.8, 100.7) |
| A6a-5B-40-1 | Initial | 100.7 (102.7, 98.6) |
| | 6 months | 98.1 (98.1, 98.0) |
| A6a-5B-40-3 | Initial | 100.7 (102.7, 98.6) |
| | 6 months | 99.2 (99.7, 98.6) |
| B7-5B-10-2 | Initial | 97.9 (98.5, 97.2) |
| | 6 months | 98.6 (97.9, 99.3) |
| B7-9-10-2 | Initial | 96.6 (93.1, 100.1)* |
| | 6 months | 95.6 (93.4, 97.8) |
| B6-5B-40-2 | Initial | 96.6 (95.2, 97.9) |
| | 6 months | 97.7 (97.3, 98.1) |
| B6-5B-40-4 | Initial | 96.6 (95.2, 97.9) |
| | 6 months | 98.3 (97.3, 99.2) |

TABLE 7

Diketopiperazine (DKP) assay.

| Sample | Time Point | DKP (%) (Replicate results shown in brackets) |
|---|---|---|
| A6a-9-40-1 | Initial | Not detected |
| | 6 months | <0.05 (<0.05, <0.05) |
| A6a-9-40-3 | Initial | Not detected |
| | 6 months | <0.05 (<0.05, <0.05) |
| A6a-5B-40-1 | Initial | Not detected |
| | 6 months | <0.05 (<0.05, <0.05) |
| A6a-5B-40-3 | Initial | Not detected |
| | 6 months | <0.05 (<0.05, <0.05) |
| B7-5B-10-2 | Initial | Not detected |
| | 6 months | 0.08 (0.08, 0.07) |
| B7-9-10-2 | Initial | Not detected |
| | 6 months | 0.07 (0.07, 0.07) |
| B6-5B-40-2 | Initial | Not detected |
| | 6 months | 0.06 (0.06, 0.06) |
| B6-5B-40-4 | Initial | Not detected |
| | 6 months | 0.05 (0.05, 0.05) |

TABLE 8a

Formulations of Table 8b.

| Reference | Formulation | Strength (mg lisinopril) | Desiccant Mass (g) |
|---|---|---|---|
| A6a-10-2 | A6a | 10 | 2 |
| A6a-40-3 | | 40 | 3 |
| B6-10-2 | B6 | 10 | 2 |
| B6-40-3 | | 40 | 3 |

TABLE 8b

Dissolution of selected IEM TAB formulations.

Mean Result (% dissolved)
(Range shown in brackets)

| Time Point (min) | A6a-10-2 Initial | A6a-10-2 6 months | A6a-40-3 Initial | A6a-40-3 6 months | B6-10-2 Initial | B6-10-2 6 months | B6-40-3 Initial | B6-40-3 6 months |
|---|---|---|---|---|---|---|---|---|
| 5 | 48.3 (43.4-56.2) | 58.3 (52.1-67.1) | 39.1 (33.7-46.5) | 49.3 (42.5-55.6) | 76.5 (65.7-86.7) | 84.3 (80.1-95.4) | 76.7 (69.6-80.2) | 84.4 (72.7-89.9) |
| 10 | 93.9 (91.1-97.1) | 96.7 (93.8-101.9) | 89.4 (74.9-99.0) | 88.7 (85.3-92.8) | 87.6 (81.7-90.1) | 92.3 (88.4-97.9) | 87.2 (80.3-93.2) | 90.5 (81.8-94.0) |

TABLE 8b-continued

Dissolution of selected IEM TAB formulations.

| | Mean Result (% dissolved) (Range shown in brackets) | | | | | | | |
|---|---|---|---|---|---|---|---|---|
| | A6a-10-2 | | A6a-40-3 | | B6-10-2 | | B6-40-3 | |
| Time Point (min) | Initial | 6 months | Initial | 6 months | Initial | 6 months | Initial | 6 months |
| 15 | 98.1 (97.2-100.1) | 101.4 (98.3-105.9) | 98.6 (86.9-106.8) | 93.4 (90.9-96.3) | 89.2 (84.3-93.1) | 94.5 (89.7-99.1) | 91.2 (84.0-96.4) | 93.1 (85.6-96.8) |
| 30 | 97.8 (97.0-99.2) | 103.1 (100.6-106.4) | 102.5 (95.3-107.1) | 96.2 (93.2-98.3) | 92.5 (89.4-96.8) | 96.9 (92.2-100.6) | 94.9 (88.8-98.0) | 95.3 (89.8-98.9) |

TABLE 9

| Sample | Time Point | Mean Result (% label claim) (Replicate results shown in brackets) |
|---|---|---|
| A6a-10-2 | Initial | 99.8 (98.7, 100.8) |
| | 6 months | 97.7 (96.4, 99.0) |
| A6a-40-3 | Initial | 102.8 (102.2, 103.3) |
| | 6 months | 96.8 (96.6, 97.0) |
| B6-10-2 | Initial | 93.3 (92.6, 93.9) |
| | 6 months | 93.6 (93.8, 93.4) |
| B6-40-3 | Initial | 100.1 (99.3, 100.8) |
| | 6 months | 96.9 (97.3, 96.4) |

TABLE 10

| Sample | Time Point | DKP (%) (Replicate results shown in brackets) |
|---|---|---|
| A6a-10-2 | Initial | Not detected |
| | 6 months | 0.17 (0.18, 0.16) |
| A6a-40-3 | Initial | Not detected |
| | 6 months | 0.18 (0.19, 0.17) |
| B6-10-2 | Initial | Not detected |
| | 6 months | 0.28 (0.28, 0.28) |
| B6-40-3 | Initial | Not detected |
| | 6 months | 0.24 (0.24, 0.24) |

Example 12 Mechanical Stability Analysis

Figure 10:
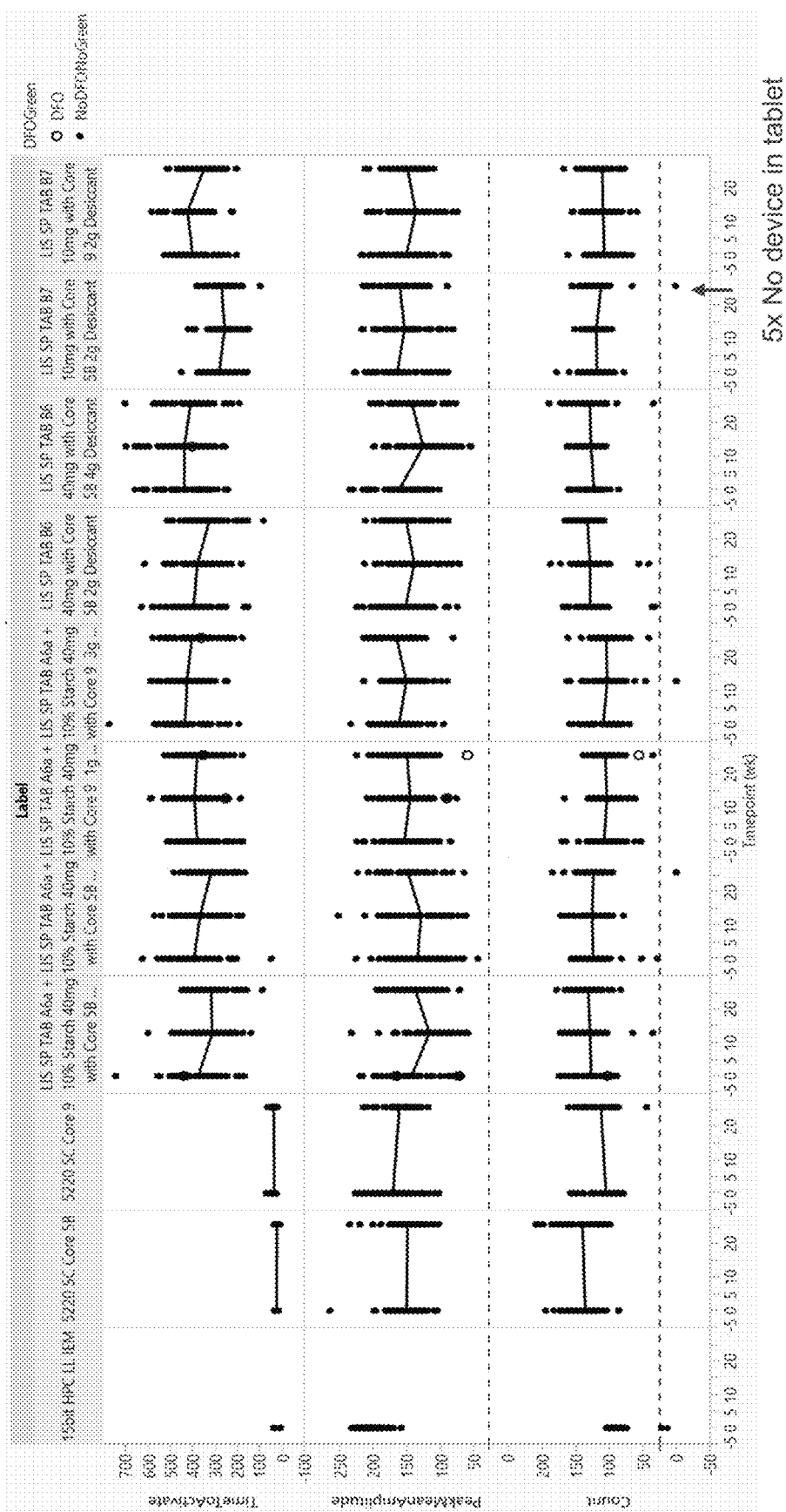
FIG. 10 shows the change in time to activation over 6 months of an ingestible event marker in certain of the SP-TAB lisinopril compositions provided herein.
Figure 11:
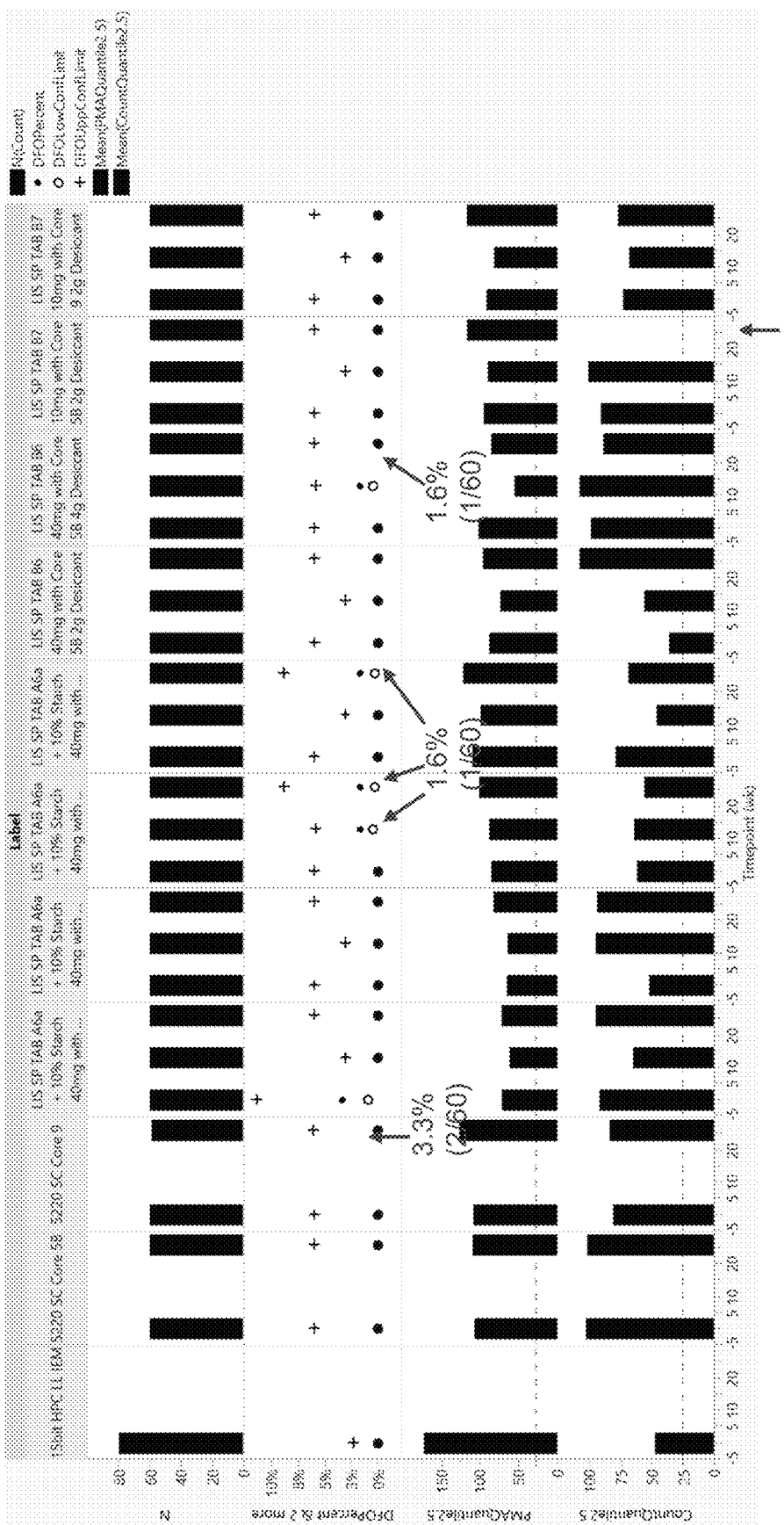
FIG. 11 shows the change in die fall-out percentage over six months of an ingestible event marker in certain of the SP-TAB lisinopril compositions provided herein.
Figure 12:
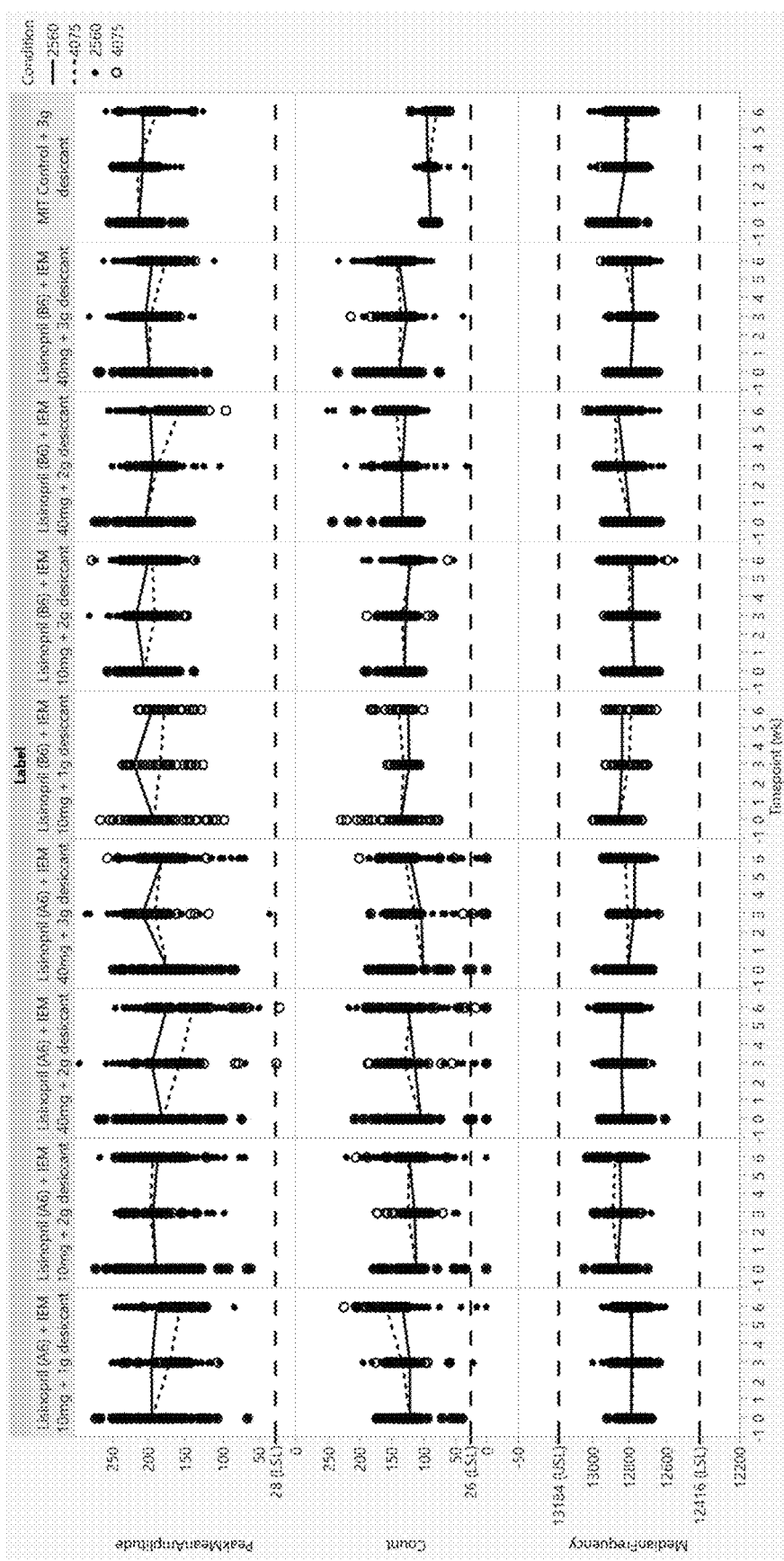
FIG. 12 shows the change in time to activation over 6 months of an ingestible event marker in certain of the IEM-TAB lisinopril compositions provided herein; "2560" corresponds to 25° C./60% relative humidity (RH), and "4075" corresponds to 40° C./75% RH.
Figure 13:
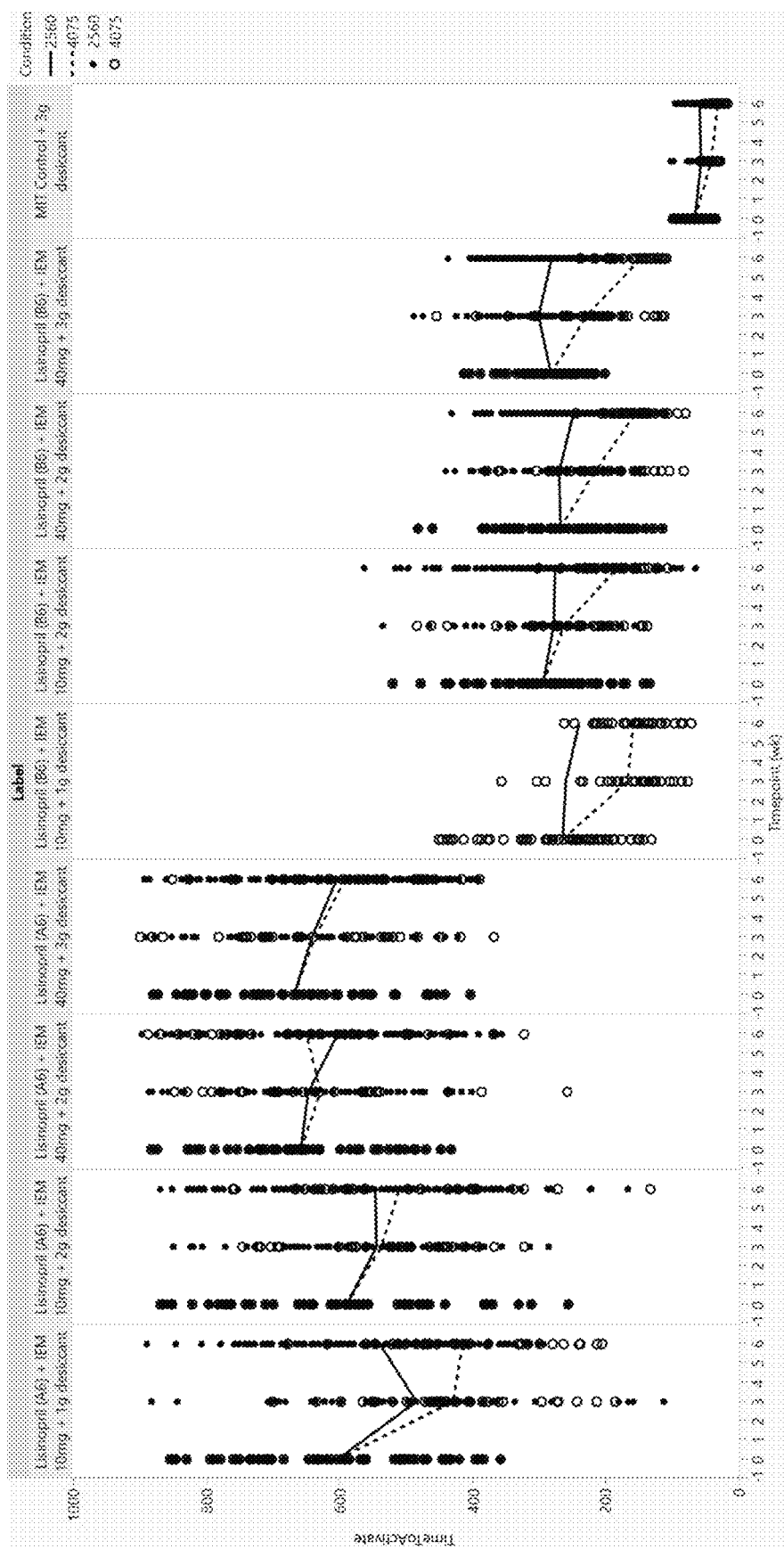
FIG. 13 shows the change in die fall-out percentage over six months of an ingestible event marker in certain of the IEM-TAB lisinopril compositions provided herein; "2560" corresponds to 25° C./60% relative humidity (RH), and "4075" corresponds to 40° C./75% RH.

The mechanical stability of certain of the compositions provided herein was assessed when configured in an ingestible form (e.g., IEM-TAB, SP-TAB, or SP-CAP). Compositions comprising lisinopril in SP-TAB using both A6 and B6 blends pass ACF specifications out to at least 6 months at both 10 mg and 40 mg dose strength at all tested desiccation levels (e.g., 1-4 g desiccant) at 25° C./60% relative humidity (RH) packaged conditions (see FIG. 10); low percentage stochastic die fall-out (DFO) was observed at some time points (see FIG. 11). Compositions comprising lisinopril in IEM-TAB using B6 blend passed ACF specifications out to at least 6 months at both 10 mg and 40 mg dose strength at all tested desiccation levels at 25° C./60% relative humidity (RH) packaged conditions, whereas A6 blend had multiple failures (see FIG. 12); B6 blend also had substantially lower activation times than A6 blend, and these activation times decline more steeply under accelerated conditions (i.e. 40° C./75% RH) (see FIG. 13). ACF stands for amplitude, count and frequency. The ACF specification was set to ensure the signals from IEM were received with a high degree of confidence. Amplitude corresponds to the strength of the signal (data packet), count is the total number of successfully sent data packets, and frequency refers to the rate at which the data packets are being sent.

It is to be understood that this disclosure is not limited to particular embodiments described, as such may vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

Although the foregoing disclosure has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the disclosure. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

What is claimed is:

1. An ingestible composition comprising:
   1) about 10% w/w lisinopril;
      about 15% w/w dicalcium phosphate, dihydrate;
      about 53.85% w/w mannitol (50 um);
      about 10% w/w pregelatinized starch; OR
   2) about 7.3% w/w lisinopril;
      about 30% w/w dicalcium phosphate, dihydrate;
      about 24.6% w/w mannitol (50 um);
      about 20% w/w pregelatinized starch; OR
   3) about 10.21% w/w lisinopril;
      about 15.31% w/w dicalcium phosphate, dihydrate;
      about 58.02% w/w mannitol (180 um);
      about 15.31% w/w pregelatinized starch; OR
   4) about 9.69% w/w lisinopril;
      about 14.53% w/w dicalcium phosphate, dihydrate;
      about 55.09% w/w mannitol (180 um);
      about 14.53% w/w pregelatinized starch; OR
   5) about 9.18% w/w lisinopril;
      about 13.76% w/w dicalcium phosphate, dihydrate;
      about 52.16% w/w mannitol (180 um);
      about 13.76% w/w pregelatinized starch; OR
   6) about 18.18% w/w lisinopril;
      about 1318% w/w dicalcium phosphate, dihydrate;
      about 47.59% w/w mannitol (50 um);
      about 10% w/w pregelatinized starch; OR
   7) about 18.18% w/w lisinopril;
      about 14.32% w/w dicalcium phosphate, dihydrate;
      about 51.36% w/w mannitol (50 um);
      about 5% w/w pregelatinized starch; OR
   8) about 7.27% w/w lisinopril;
      about 30% w/w dicalcium phosphate, dihydrate;
      about 24.58% w/w mannitol (50 um);
      about 20% w/w pregelatinized starch; OR
   9) about 10% w/w lisinopril;
      about 28% w/w dicalcium phosphate, dihydrate;
      about 22.85% w/w mannitol (50 um);
      about 20% w/w pregelatinized starch; OR
   10) about 10.26% w/w lisinopril;
      about 15.38% w/w dicalcium phosphate, dihydrate;
      about 58.32% w/w mannitol (180 um);
      about 15.38% w/w pregelatinized starch; OR
   11) about 10.16% w/w lisinopril;
      about 15.23% w/w dicalcium phosphate, dihydrate;
      about 57.73% w/w mannitol (180 um);
      about 15.23% w/w pregelatinized starch; OR
   12) about 10.05% w/w lisinopril;
      about 15.07% w/w dicalcium phosphate, dihydrate;
      about 57.14% w/w mannitol (180 um);
      about 15.07% w/w pregelatinized starch; OR
   13) about 10.1% w/w lisinopril;
      about 15.15% w/w dicalcium phosphate, dihydrate;
      about 57.44% w/w mannitol (180 um);
      about 15.15% w/w pregelatinized starch; OR
   14) about 10% w/w lisinopril;
      about 15% w/w dicalcium phosphate, dihydrate;
      about 56.85% w/w mannitol (180 um);
      about 15% w/w pregelatinized starch; OR
   15) about 9.74% w/w lisinopril;
      about 14.61% w/w dicalcium phosphate, dihydrate;
      about 55.39% w/w mannitol (180 um);
      about 14.61% w/w pregelatinized starch; OR
   16) about 10.62% w/w lisinopril;
      about 15.92% w/w dicalcium phosphate, dihydrate;
      about 57.18% w/w mannitol (180 um);
      about 10.62% w/w pregelatinized starch; OR
   17) about 10.06% w/w lisinopril;
      about 15.08% w/w dicalcium phosphate, dihydrate;
      about 54.16% w/w mannitol (180 um);
      about 10.06% w/w pregelatinized starch; and
   an ingestible identifier comprising:
      an integrated circuit comprising silicon, aluminum, silicon dioxide, and silicon nitride;
      a wafer comprising titanium, titanium-tungsten, gold, magnesium, copper (I) chloride, and hydroxypropyl cellulose; and
      a skirt film comprising ethyl cellulose, hydroxypropyl cellulose, and triethyl citrate.

2. The ingestible composition of claim 1, wherein the ingestible composition further comprises iron oxide yellow or water, or both.

3. The ingestible composition of claim 1, wherein the ingestible composition comprises about 0.10% to about 0.20% w/w iron oxide yellow.

4. The ingestible composition of claim 1, wherein the ingestible composition comprises about 0.10% to about 0.15% w/w iron oxide yellow.

5. The ingestible composition of claim 1, wherein the ingestible composition comprises about 0.15% to about 0.20% w/w iron oxide yellow.

6. The ingestible composition of claim 1, wherein the ingestible composition comprises about 0.15% w/w iron oxide yellow.

7. The ingestible composition of claim 1, wherein the ingestible composition comprises:
   about 0% to about 30.0% w/w microcrystalline cellulose;
   about 0% to about 2.5% w/w croscarmellose sodium;

about 0% to about 0.20% w/w iron oxide; and about 0% to about 0.30% w/w FD&C yellow #6.

8. The ingestible composition of claim 7, wherein the comprises about 0 or 16% w/w microcrystalline cellulose.

9. The ingestible composition of claim 8, wherein the ingestible composition comprises about 0 or 2% w/w croscarmellose sodium.

10. The ingestible composition of claim 9, wherein the ingestible composition comprises about 0.14 or 0.15% w/w iron oxide.

11. The ingestible composition of claim 10, wherein the ingestible composition comprises about 0% w/w FD&C yellow #6.

* * * * *